(12) United States Patent
Aratake et al.

(10) Patent No.: US 8,163,512 B2
(45) Date of Patent: Apr. 24, 2012

(54) METHOD FOR DETERMINATION OF CHOLESTEROL IN SMALL DENSE LOW-DENSITY LIPOPROTEIN

(75) Inventors: Tomoko Aratake, Shizuoka (JP); Yuki Katayama, Shizuoka (JP); Shingo Mishima, Shizuoka (JP)

(73) Assignee: Kyowa Medex Co., Ld., Tokyo (JP)

( * ) Notice: Subject to any disclaimer, the term of this patent is extended or adjusted under 35 U.S.C. 154(b) by 292 days.

(21) Appl. No.: 12/377,318

(22) PCT Filed: Oct. 16, 2007

(86) PCT No.: PCT/JP2007/070172
§ 371 (c)(1),
(2), (4) Date: May 12, 2009

(87) PCT Pub. No.: WO2008/050636
PCT Pub. Date: May 2, 2008

(65) Prior Publication Data
US 2010/0041080 A1    Feb. 18, 2010

(30) Foreign Application Priority Data

Oct. 18, 2006    (JP) .................................. 2006-283418

(51) Int. Cl.
*C12Q 1/60*    (2006.01)
(52) U.S. Cl. ......................................................... 435/11
(58) Field of Classification Search ...................... 435/11
See application file for complete search history.

(56) References Cited

U.S. PATENT DOCUMENTS

| | | |
|---|---|---|
| 6,794,157 B1 | 9/2004 | Sugiuchi |
| 2006/0154374 A1 | 7/2006 | Itoh et al. |
| 2009/0246807 A1* | 10/2009 | Sun ................................. 435/11 |

FOREIGN PATENT DOCUMENTS

| | | |
|---|---|---|
| EP | 1 114 870 | 7/2001 |
| EP | 1 571 452 | 9/2005 |
| EP | 1 930 442 | 6/2008 |
| JP | 2000-325097 | 11/2000 |
| JP | 2003-028882 | 1/2003 |
| JP | 2006-226913 | 8/2006 |
| WO | 00/17388 | 3/2000 |
| WO | 2004-053500 | 6/2004 |
| WO | 2007-001011 | 1/2007 |
| WO | 2007-026829 | 3/2007 |
| WO | 2007/066760 | 6/2007 |

OTHER PUBLICATIONS

Lamarche B. et al. Small, Dense Low Density Lipoprotein Particles as a Predictor of the Risk of Ischemic Heart Disease in Men. Circulation Jan. 7, 1997, 95(1)69-75.*
Wang H. et al. Microchip Based Small, Dense Low Density Lipoproteins Assay for Coronary Heart Disease Risk Assessment. Electrophoresis 29, 1932-1941, 2008.*
Hirano, et al., "Measurement of Small Dense Low-density Lipoprotein Particles", J. Atherosclerosis and Thrombosis, vol. 12, No. 2 (2005) 67-72.

* cited by examiner

*Primary Examiner* — Ralph Gitomer
(74) *Attorney, Agent, or Firm* — Fitzpatrick, Cella, Harper & Scinto

(57) ABSTRACT

A method for determination of sdLDL-C in a reaction solution containing a surfactant that preferentially inhibits the reaction of sdLDL-C with enzymes for cholesterol measurement such as cholesterol ester hydrolase. In the method, the enzymes for cholesterol measurement act on a sample to eliminate HDL-C, VLDL-C, CM-C and LgLDL-C. A reagent that causes the reaction of sdLDL-C remaining in the reaction solution to form hydrogen peroxide or reduced coenzyme is then added, following which the formed hydrogen peroxide or reduced coenzyme is measured. The sdLDL-C concentration in the sample may be determined by comparing the measurement value with and a previously-prepared calibration curve.

3 Claims, No Drawings

METHOD FOR DETERMINATION OF CHOLESTEROL IN SMALL DENSE LOW-DENSITY LIPOPROTEIN

TECHNICAL FIELD

The present invention relates to a method and a kit for determination of cholesterol in a small dense low-density lipoprotein (hereinafter abbreviated as sdLDL) (hereinafter abbreviated as sdLDL-C) in a sample.

BACKGROUND ART

Lipoproteins present in blood are roughly classified into four classes: high-density lipoprotein (hereinafter abbreviated as HDL), low-density lipoprotein (hereinafter abbreviated as LDL), very low-density lipoprotein (hereinafter abbreviated as VLDL) and chylomicron (hereinafter abbreviated as CM) according to their specific gravity. Each class of lipoprotein has a different lipid composition and also has a considerably different function in vivo according to the kind of apoproteins constituting each lipoprotein. Also there exists, as a lipoprotein formed in the process of metabolism from VLDL to LDL, intermediate-density lipoprotein (hereinafter abbreviated as IDL) having a density between those of VLDL and LDL, which is classified as LDL in a broad sense.

In clinical tests, total cholesterol, total triglyceride, HDL cholesterol, LDL cholesterol, apolipoprotein AI, apolipoprotein B, etc. are used as a screening marker for diagnosis of arteriosclerosis. In particular, the frequency of measurement of cholesterol in LDL, which is said to be strongly associated with the formation of arteriosclerosis, has been increasing. On the other hand, there observed many patients having coronary arteriosclerotic lesion without showing a high LDL cholesterol level. In such cases, increase of small and high-density LDL (this LDL is called sdLDL) is observed, and there is a report that sdLDL-C is more closely associated with coronary diseases than LDL-C [see Arteriosclerosis Thrombosis, and Vascular Biology, Vol. 24, p. 558-563 (2004)].

Known examples of methods for measuring sdLDL include the electrophoresis method, the ultracentrifugation method and the fractionation method. The electrophoresis method is a method which comprises carrying out electrophoresis and staining using 2 to 16% non-denatured gradient gel to measure the particle size of LDL, but it involves complicated operations and is unsuitable for wide use. Further, this method is capable of measuring the particle size of LDL but is incapable of determining sdLDL. Also known is a method in which sdLDL is suspended or dissolved according to the difference in ionic strength and sdLDL is measured based on the difference in absorbance (see patent document 1). However, being based on the measurement of turbidity, this method is insufficient in specificity and accuracy, and further, it is capable of measuring the amount of sdLDL but is incapable of measuring sdLDL-C.

Known examples of methods for determining sdLDL-C include the ultracentrifugation method and the fractionation method. The ultracentrifugation method is a method which comprises separating a specific gravity region corresponding to sdLDL in a sample using an ultracentrifuge and measuring cholesterol in the specific gravity region, and it can be a standard method for determination of sdLDL-C. However, this method requires expensive equipments and also requires a very long measurement time and operation skill.

The fractionation method is a method which comprises a first step in which lipoproteins other than HDL and sdLDL in a sample are aggregated using a combination of polyanion and a divalent cation or a monovalent cation, or polyethylene glycol, and the aggregated lipoproteins are removed by centrifugation or filtration using a filter to separate HDL and sdLDL, and a second step in which sdLDL-C in the sample containing the separated HDL and sdLDL is determined (see patent document 2). Although this method can be performed with simplified operations compared with the ultracentrifugation method, it requires a long measurement time because of the necessity of a fractionation operation.

There are many reports on the methods for measuring cholesterol in a specific lipoprotein to be measured by allowing a cholesterol ester hydrolase and cholesterol oxidase or cholesterol dehydrogenase to act specifically on one or plural specific lipoproteins selected from the group consisting of HDL, LDL, VLDL and CM in the presence of surfactants. Recently, there has been reported a method for determination of sdLDL-C which comprises adding enzymes for measurement of cholesterol to a sample in the presence of a polyoxyethylene-polyoxypropylene copolymer or its derivative, allowing the polyoxyethylene-polyoxypropylene copolymer or its derivative to act selectively on sdLDL, and measuring the amount of formed cholesterol (patent document 3).

Patent document 1: Japanese Laid-Open Patent Publication No. 2003-28882
Patent document 2: WO2004/053500 pamphlet
Patent document 3: WO2007/026829 pamphlet

DISCLOSURE OF THE INVENTION

Object to be Solved by the Invention

An object of the present invention is to provide a method and a kit for simple and accurate determination of sdLDL-C in a sample.

Means to Solve the Object

The present invention relates to the following [1] to [12].
[1] A method for determining cholesterol in a small dense low-density lipoprotein (hereinafter abbreviated as sdLDL-C) in a sample, which comprises the following steps (i), (ii) and (iii):
(i) in a reaction solution containing a surfactant (hereinafter referred to as surfactant A) which preferentially inhibits the reaction of sdLDL-C with cholesterol ester hydrolase and cholesterol oxidase, or cholesterol ester hydrolase, cholesterol dehydrogenase and oxidized coenzyme compared with the reaction of cholesterol in high-density lipoprotein (hereinafter abbreviated as HDL-C), cholesterol in very low-density lipoprotein (hereinafter abbreviated as VLDL-C), cholesterol in chylomicron (hereinafter abbreviated as CM-C) and cholesterol in large low-density lipoprotein (hereinafter abbreviated as LgLDL-C) with cholesterol ester hydrolase and cholesterol oxidase, or cholesterol ester hydrolase, cholesterol dehydrogenase and oxidized coenzyme, allowing cholesterol ester hydrolase and cholesterol oxidase, or cholesterol ester hydrolase, cholesterol dehydrogenase and oxidized coenzyme to act on the sample to eliminate HDL-C, VLDL-C, CM-C and LgLDL-C in the sample;
(ii) adding a reagent which causes a reaction of sdLDL-C remaining in the reaction solution containing surfactant A of the above step (i) with cholesterol ester hydrolase and cholesterol oxidase, or cholesterol ester hydrolase, cholesterol dehydrogenase and oxidized coenzyme to form hydrogen peroxide or reduced coenzyme, and measuring the formed hydrogen peroxide or reduced coenzyme; and (iii) determining a sdLDL-C concentration in the sample by carrying out the above steps (i) and (ii) using a standard sample with a known concentration of sdLDL-C to form hydrogen peroxide or reduced coenzyme, measuring the formed hydrogen peroxide or reduced coenzyme, correlating the sdLDL-C concentration with a measurement value on the hydrogen peroxide or reduced coenzyme, thereby to determine a sdLDL-C concentration in the sample.

[2] The method according to [1], wherein the reagent which causes a reaction of sdLDL-C remaining in the reaction solution containing surfactant A of step (i) with cholesterol ester hydrolase and cholesterol oxidase, or cholesterol ester hydrolase, cholesterol dehydrogenase and oxidized coenzyme is a surfactant (hereinafter referred to as surfactant B) which releases the inhibition of the reaction of sdLDL-C with cholesterol ester hydrolase and cholesterol oxidase, or cholesterol ester hydrolase, cholesterol dehydrogenase and oxidized coenzyme.

[3] The method according to [1] or [2], wherein surfactant A is a surfactant selected from the group consisting of polyoxyethylene alkylamine, amine oxide, alkylbetaine, alkylammonio-1-propanesulfonate, acid amide alkylbetaine, polyoxyethylene benzyl alkyl quaternary ammonium salt, polyoxyethylene fatty acid amide, polyoxyethylene polycyclic phenyl ether sulfuric acid ester salt, polyoxyethylene alkylphenyl ether sulfuric acid ester salt, polyoxyethylene fatty acid amide sulfuric acid ester salt, polyoxyethylene alkylamine sulfuric acid ester salt, N-acyl taurine salt, N-acyl amino acid salt, ethylenediamine-polyoxyethylene polyoxypropylene condensate, polypropylene glycol derivative not including polyethylene glycol therein, polyoxyethylene polyoxypropylene condensate represented by general formula (I):

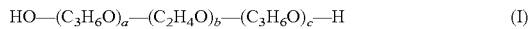

$$HO-(C_3H_6O)_a-(C_2H_4O)_b-(C_3H_6O)_c-H \qquad (I)$$

(wherein a, b and c, which may be the same or different, each represents an integer of 1 to 200), and polyoxyethylene polyoxyalkylene alkyl ether (the alkyl is an alkyl having 9 or less carbon atoms).

[4] The method according to any one of [1] to [3], wherein surfactant B is a surfactant selected from the group consisting of polyoxyethylene alkyl ether, polyoxyethylene polyoxyalkylene alkyl ether (the alkyl is an alkyl having 10 or more carbon atoms), polyoxyethylene alkylphenyl ether, polyoxyethylene polyoxyalkylene alkylphenyl ether, polyoxyethylene polycyclic phenyl ether, polyoxyethylene polyoxyalkylene polycyclic phenyl ether, polyoxyethylene polyoxypropylene condensate represented by general formula (II):

$$HO-(C_2H_4O)_d-(C_3H_6O)_e-(C_2H_4O)_f-H \qquad (II)$$

(wherein d, e and f, which may be the same or different, each represents an integer of 1 to 200), and polyoxyethylene polyoxyalkylene alkylamine.

[5] The method according to any one of [1] to [4], wherein step (i) is carried out in the presence of albumin.

[6] A kit for determining cholesterol in a small dense low-density lipoprotein (hereinafter abbreviated as sdLDL-C) in a sample, which comprises (a) a first reagent comprising a surfactant (hereinafter referred to as surfactant A) which preferentially inhibits a reaction of sdLDL-C with cholesterol ester hydrolase and cholesterol oxidase or cholesterol ester hydrolase, cholesterol dehydrogenase and oxidized coenzyme compared with a reaction of cholesterol in high-density lipoprotein, cholesterol in very low-density lipoprotein, cholesterol in chylomicron and cholesterol in large low-density lipoprotein with cholesterol ester hydrolase and cholesterol oxidase, or cholesterol ester hydrolase, cholesterol dehydrogenase and oxidized coenzyme; cholesterol ester hydrolase: cholesterol oxidase and a reagent for eliminating hydrogen peroxide, and (b) a second reagent comprising a reagent which causes a reaction of sdLDL-C with cholesterol ester hydrolase and cholesterol oxidase, or cholesterol ester hydrolase, cholesterol dehydrogenase and oxidized coenzyme in the copresence of surfactant A and a reagent for measuring hydrogen peroxide.

[7] A kit for determining cholesterol in a small dense low-density lipoprotein (hereinafter abbreviated as sdLDL-C) in a sample, which comprises (a) a first reagent comprising a surfactant (hereinafter referred to as surfactant A) which preferentially inhibits a reaction of sdLDL-C with cholesterol ester hydrolase and cholesterol oxidase, or cholesterol ester hydrolase, cholesterol dehydrogenase and oxidized coenzyme compared with a reaction of cholesterol in high-density lipoprotein, cholesterol in very low-density lipoprotein, cholesterol in chylomicron and cholesterol in large low-density lipoprotein with cholesterol ester hydrolase and cholesterol oxidase, or cholesterol ester hydrolase, cholesterol dehydrogenase and oxidized coenzyme; cholesterol ester hydrolase; oxidized coenzyme and cholesterol dehydrogenase, and (b) a second reagent comprising a reagent which causes the reaction of sdLDL-C with a cholesterol ester hydrolase and cholesterol oxidase or a cholesterol ester hydrolase and cholesterol dehydrogenase-oxidized coenzyme in the copresence of surfactant A.

[8] The kit according to [6] or [7], wherein the reagent which causes a reaction of sdLDL-C with cholesterol ester hydrolase and cholesterol oxidase, or cholesterol ester hydrolase, cholesterol dehydrogenase and oxidized coenzyme in the copresence of surfactant A is a surfactant (hereinafter referred to as surfactant B) which releases the inhibition of a reaction of sdLDL-C with cholesterol ester hydrolase and cholesterol oxidase, or cholesterol ester hydrolase, cholesterol dehydrogenase and oxidized coenzyme.

[9] The kit according to any one of [6] to [8], wherein surfactant A is a surfactant selected from the group consisting of polyoxyethylene alkylamine, amine oxide, alkylbetaine, alkylammonio-1-propanesulfonate, acid amide alkylbetaine, polyoxyethylene benzyl-alkyl quaternary ammonium salt, polyoxyethylene fatty acid amide, polyoxyethylene polycyclic phenyl ether sulfuric acid ester salt, polyoxyethylene alkylphenyl ether sulfuric acid ester salt, polyoxyethylene fatty acid amide sulfuric acid ester salt, polyoxyethylene alkylamine sulfuric acid ester salt, N-acyl taurine salt, N-acyl amino acid salt, ethylenediamine-polyoxyethylene polyoxypropylene condensate, polypropylene glycol derivative not including polyethylene glycol therein, polyoxyethylene polyoxypropylene condensate represented by general formula (I):

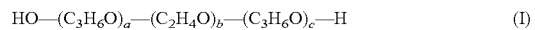

$$HO-(C_3H_6O)_a-(C_2H_4O)_b-(C_3H_6O)_c-H \qquad (I)$$

(wherein a, b and c, which may be the same or different, each represents an integer of 1 to 200), and polyoxyethylene polyoxyalkylene alkyl ether (the alkyl is an alkyl having 9 or less carbon atoms).

[10] The kit according to any one of [6] to [9], wherein surfactant B is a surfactant selected from the group consisting of polyoxyethylene alkyl ether, polyoxyethylene polyoxyalkylene alkyl ether (the alkyl is an alkyl having 10 or more carbon atoms), polyoxyethylene alkylphenyl ether, polyoxyethylene polyoxyalkylene alkylphenyl ether, polyoxyethylene polycyclic phenyl ether, polyoxy-

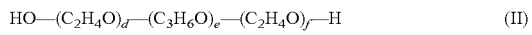

ethylene polyoxyalkylene polycyclic phenyl ether, polyoxyethylene polyoxypropylene condensates represented by general formula (II):

$$HO—(C_2H_4O)_d—(C_3H_6O)_e—(C_2H_4O)_f—H \quad (II)$$

(wherein d, e and f, which may be the same or different, each represents an integer of 1 to 200), and polyoxyethylene polyoxyalkylene alkylamine.

[11] The kit according to any one of [6] to [10], wherein albumin is contained at least in the first reagent.

[12] The kit according to any one of [6] to [11], further comprising, as a third reagent, a standard product with a known concentration of sdLDL.

Effect of the Invention

The present invention provides a method and a kit for simple and accurate determination of sdLDL-C in a sample.

BEST MODE OF CARRYING OUT THE INVENTION

The terms "HDL-C", "VLDL-C" and "CM-C" collectively refer to a combination of free cholesterol and esterified cholesterol in HDL, VLDL and CM, respectively.

Examples of the sample used in the measurement method of the present invention include whole blood, plasma, serum, spinal fluid, saliva, amniotic fluid, urine, sweat and pancreatic juice, among which plasma and serum are preferred.

There is no specific restriction as to cholesterol ester hydrolase used in the present invention as long as it is an enzyme having the ability to hydrolyze cholesterol ester. For example, cholesterol esterase and lipoprotein lipase derived from animals, plants or microorganisms, and those produced by genetic engineering techniques can be used.

As the cholesterol ester hydrolase, both unmodified ones and chemically modified ones can be used, and commercial products can also be used.

Examples of the commercially available cholesterol ester hydrolases include cholesterol esterase "Amano" 2 (CHE2; Amano Enzyme Inc.), cholesterol esterase "Amano" 3 (CHE3; Amano Enzyme Inc.), lipoprotein lipase "Amano" 3 (LPL3; Amano Enzyme Inc.), lipoprotein lipase (LPL-311; Toyobo Co., Ltd.), lipoprotein lipase (LPL-312; Toyobo Co., Ltd.), cholesterol esterase (COE-301; Toyobo Co., Ltd.), lipoprotein lipase (LPBP; Asahi Kasei Corporation), cholesterol esterase (CEBP-M; Asahi Kasei Corporation), cholesterol esterase (CEN; Asahi Kasei Corporation), lipase (LP; Asahi Kasei Corporation), lipase (LPM; Asahi Kasei Corporation), lipase (LPAP; Asahi Kasei Corporation), lipase (LIPS; Asahi Kasei Corporation) and cholesterol esterase (CHE-BE; Kikkoman Corporation). In the present invention, two or more kinds of cholesterol ester hydrolases can be used in combination.

Examples of the group modifying cholesterol ester hydrolase (chemically modifying group) in the chemically modified cholesterol ester hydrolase include a group comprising polyethylene glycol as a main component, a group comprising polypropylene glycol as a main component, a group having a copolymer of polypropylene glycol and polyethylene glycol, a group comprising a water-soluble polysaccharide, a sulfopropyl group, a sulfobutyl group, a polyurethane group and a group having a chelating function, and preferred is a group comprising polyethylene glycol as a main component. Examples of the water-soluble polysaccharides include dextran, pullulan and soluble starch.

Examples of the reagent for chemical modification of cholesterol ester hydrolase (chemical modifier) include compounds that have both the above chemically modifying group and a functional group or a structure which can react with an amino group, a carboxyl group, a sulfhydryl group or the like of an enzyme. Examples of the functional group or structure which can react with an amino group of an enzyme include a carboxyl group, an activated ester group (e.g., N-hydroxysuccinimide group), an acid anhydride, an acid chloride, an aldehyde, an epoxide group, 1,3-propanesultone and 1,4-butanesultone. An example of the functional group or structure which can react with a carboxyl group of an enzyme is an amino group. Examples of the group or structure which can react with a sulfhydryl group of an enzyme include a maleimide group, a disulfide and α-haloester (e.g., α-iodo ester).

As the chemical modifier, commercial products can also be used. Examples of the commercially available chemical modifier include Sunbright VFM-4101, Sunbright ME-050AS and Sunbright DE-030AS (all produced by NOF Corporation) which have a group comprising polyethylene glycol as a main component and an N-hydroxysuccinimide group, Sunbright AKM series (e.g., Sunbright AKM-1510), Sunbright ADM series and Sunbright ACM series (all produced by NOF Corporation) which have a group comprising polyalkylene glycol such as polyethylene glycol or polypropylene glycol as a main component and an acid anhydride structure, EPOX-3400 and M-EPOX-5000 (both produced by Sheawater Polymers) which have a group comprising polyethylene glycol as a main component and an epoxide group, and diethylenetriamine-N,N,N',N'',N''-pentaacetic dianhydride which has a group having a chelating function and an acid anhydride structure (DTPA anhydride, Dojindo Laboratories).

Chemical modification of cholesterol ester hydrolase can be carried out, for example, by the following method, but is not limited thereto. First, cholesterol ester hydrolase is dissolved in a buffer of pH 8.0 or higher {e.g., 2-[4-(2-hydroxyethyl)-1-piperazinyl]ethanesulfonic acid (HEPES) buffer}, and 0.01 to 500-fold molar amount of a chemical modifier is added thereto at 0 to 55° C., followed by stirring for 5 minutes to 5 hours. In the actual enzymatic reaction, this reaction solution can be used as such, or if necessary, after removal of the unreacted chemical modifier or the like with an ultrafilter membrane or the like, as the chemically modified cholesterol ester hydrolase.

There is no specific restriction as to the concentration of cholesterol ester hydrolase used in the method of the present invention, as long as the determination of sdLDL-C according to the present invention can be performed. Its concentration in a reaction solution is preferably 0.001 to 2000 U/mL, more preferably 0.005 to 1000 U/mL.

There is no specific restriction as to the cholesterol oxidase used in the present invention as long as it is an enzyme having an ability to oxidize cholesterol to form a hydrogen peroxide. For example, cholesterol oxidase derived from animals, plants or microorganisms, and those produced by genetic engineering techniques can be used. Commercial products such as cholesterol oxidase "Amano" 1 (CHOD1; Amano Enzyme Inc.), cholesterol oxidase (CHO-PEL; Kikkoman Corporation), cholesterol oxidase (CHO-PEWL; Kikkoman Corporation), cholesterol oxidase (CHO-CE; Kikkoman Corporation), cholesterol oxidase (COO321; Toyobo Co., Ltd.) and cholesterol oxidase (COO322; Toyobo Co., Ltd.) can also be used. In the present invention, two or more kinds of cholesterol oxidases can be used in combination.

Cholesterol oxidase may be either an unmodified enzyme or a chemically modified enzyme. Chemically modified cholesterol oxidase can be prepared, for example, by the above method for chemical modification using the above chemical modifier.

There is no specific restriction as to the concentration of cholesterol oxidase used in the method of the present invention, as long as the determination of sdLDL-C according to the present invention can be performed. Its concentration in a reaction solution is preferably 0.001 to 2000 U/mL, more preferably 0.005 to 1000 U/mL.

There is no specific restriction as to the cholesterol dehydrogenase used in the present invention as long as it is an enzyme having an ability to oxidize cholesterol in the presence of oxidized coenzyme to form a reduced coenzyme. For example, cholesterol dehydrogenase derived from animals, plants or microorganisms, and those produced by genetic engineering techniques can be used. Commercial products such as cholesterol dehydrogenase "Amano" 5 (CHDH5; Amano Enzyme Inc.) can also be used. In the present invention, two or more kinds of cholesterol dehydrogenases can be used in combination.

Cholesterol dehydrogenase may be either an unmodified enzyme or a chemically modified enzyme. Chemically modified cholesterol dehydrogenase can be prepared, for example, by the above method for chemical modification using the above chemical modifier.

There is no specific restriction as to the concentration of cholesterol dehydrogenase used in the method of the present invention, as long as the determination of sdLDL-C according to the present invention can be performed. Its concentration in a reaction solution is preferably 0.001 to 2000 U/mL, more preferably 0.005 to 1000 U/mL.

Examples of the oxidized coenzyme used in the determination using cholesterol dehydrogenase are $NAD(P)^+$ and thio-$NAD(P)^+$. Examples of the reduced coenzyme formed by a reaction of cholesterol dehydrogenase with cholesterol in lipoprotein in the copresence of oxidized coenzyme are $NAD(P)H$ and thio-$NAD(P)H$.

There is no specific restriction as to the concentration of oxidized coenzyme used in the method of the present invention, as long as the determination of sdLDL-C according to the present invention can be performed. Its concentration in a reaction solution is preferably 0.01 to 400 mmol/L, more preferably 0.1 to 100 mmol/L.

In the method for determination of sdLDL-C of the present invention, reduced coenzyme oxidase can also be used. Herein, reduced coenzyme oxidase is used together with cholesterol dehydrogenase and oxidized coenzyme, and it converts reduced coenzyme formed by a reaction of cholesterol dehydrogenase with cholesterol in lipoprotein in the copresence of oxidized coenzyme into a hydrogen peroxide. An example of the reduced coenzyme oxidase is NAD(P)H oxidase. As the reduced coenzyme oxidase, commercial products can also be used. An example of the commercially available reduced coenzyme oxidase is NADH Oxidase (Cosmo Bio Co., Ltd.)

There is no specific restriction as to the concentration of reduced coenzyme oxidase used in the method of the present invention, as long as the determination of sdLDL-C according to the present invention can be performed. Its concentration in a reaction solution is preferably 0.01 to 400 U/mL, more preferably 0.02 to 200 U/mL.

There is no specific restriction as to the albumin used in the present invention as long as the determination of sdLDL-C according to the present invention can be performed. Examples of the albumin include albumin derived from cow, horse, sheep and human, where bovine serum albumin (BSA) is preferred. Albumin produced by genetic engineering techniques can also be used. In the present invention, two or more kinds of albumin can be used in combination. There is no specific restriction as to the concentration of albumin in the determination of sdLDL-C of the present invention, as long as the determination of sdLDL-C according to the present invention can be performed. Its concentration in a reaction solution is preferably 0.001 to 10%, more preferably 0.01 to 5%.

Surfactant A in the present invention has a property to inhibit the reaction of sdLDL-C with cholesterol esterase and cholesterol oxidase, or cholesterol esterase, cholesterol dehydrogenase and oxidized coenzyme and to cause the reaction of LgLDL-C. Specifically, surfactant A is a surfactant which preferentially inhibits the reaction of sdLDL-C with cholesterol ester hydrolase and cholesterol oxidase, or cholesterol ester hydrolase and cholesterol dehydrogenase and oxidized coenzyme compared with the reaction of HDL-C, VLDL-C, CM-C and LgLDL-C with cholesterol ester hydrolase and cholesterol oxidase, or cholesterol ester hydrolase, cholesterol dehydrogenase and oxidized coenzyme, and is a surfactant used for elimination of cholesterol other than sdLDL-C, that is, HDL-C, VLDL-C, CM-C and LgLDL-C in step (i). Hereinafter, HDL-C, VLDL-C, CM-C and LgLDL-C may be sometimes referred to as cholesterol in lipoproteins other than sdLDL collectively.

Examples of surfactant A include polyoxyethylene alkylamine (hereinafter abbreviated as POE alkylamine), amine oxide, alkylbetaine, alkylammonio-1-propanesulfonate, acid amide alkylbetaine, polyoxyethylene benzyl-alkyl quaternary ammonium salt (hereinafter abbreviated as POE benzyl alkyl quaternary ammonium salt), polyoxyethylene fatty acid amide (hereinafter abbreviated as POE fatty acid amide), polyoxyethylene polycyclic phenyl ether sulfuric acid ester salt (hereinafter abbreviated as POE polycyclic phenyl ether sulfuric acid ester salt), polyoxyethylene alkylphenyl ether sulfuric acid ester salt (hereinafter abbreviated as POE alkylphenyl ether sulfuric acid ester salt), polyoxyethylene fatty acid amide sulfuric acid ester salt (hereinafter abbreviated as POE fatty acid amide sulfuric acid ester salt), polyoxyethylene alkylamine sulfuric acid ester salt (hereinafter abbreviated as POE alkylamine sulfuric acid ester salt), N-acyl taurine salt, N-acyl amino acid salt, ethylenediamine-polyoxyethylene polyoxypropylene condensate (hereinafter abbreviated as ethylenediamine-POE•POP condensate), polypropylene glycol derivative not including polyethylene glycol therein (hereinafter abbreviated as PPG derivative), polyoxyethylene polyoxypropylene condensate (hereinafter abbreviated as POE-POP condensate) represented by general formula (I):

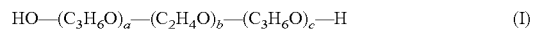

$$HO-(C_3H_6O)_a-(C_2H_4O)_b-(C_3H_6O)_c-H \qquad (I)$$

(wherein a, b and c, which may be the same or different, each represent an integer of 1 to 200), and polyoxyethylene polyoxyalkylene alkyl ether (the alkyl is alkyl having 9 or less carbon atoms) (hereinafter abbreviated as POE•POA alkyl ethers of C9 or less).

The alkyl in the POE alkylamine, alkylbetaine, alkylammonio-1-propanesulfonate, acid amide alkylbetaine, POE alkylphenyl ether sulfuric acid ester salt and POE alkylamine sulfuric acid ester salt includes alkyl groups having 1 to 30 carbon atoms, such as methyl, ethyl, propyl, butyl, pentyl, hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl and triacontyl.

Examples of commercial products of the POE alkylamine include Pionin D-3104, Pionin D-3110 and Pionin D-3120

(all produced by Takemoto Oil and Fat Co., Ltd.), Nymeen L-207 (produced by NOF Corporation) and BLAUNON L-205 (produced by Aoki Oil Industrial Co., Ltd.).

Examples of the amine oxide include alkylamine oxide and polyoxyethylene alkylamine oxide (hereinafter abbreviated as POE alkylamine oxide). The alkyl in the alkylamine oxide and POE alkylamine oxide includes, for example, substituted or unsubstituted alkyl groups having 1 to 30 carbon atoms. Examples of the alkyl include the alkyl groups mentioned above. Examples of the substituent include a hydroxyl group. Examples of the commercial products of the amine oxide include Unisafe A-LE, Unisafe A-LM and Unisafe A-LY (all produced by NOF Corporation).

Examples of commercial products of the alkylbetaines include Nissan Anon BL and Nissan Anon BF (both produced by NOF Corporation) and Amphitol 24B and Amphitol 86B (both produced by Kao Corporation).

Examples of commercial products of the alkylammonio-1-propanesulfonate include ZWITTERGENT3-10 and ZWITTERGENT3-12 (both produced by CALBIOCHEM).

Examples of commercial products of the acid amide alkylbetaine include Anon BDF-SF (produced by NOF Corporation).

Examples of commercial products of the POE benzyl alkyl quaternary ammonium salts include Bisnol SK (produced by Ipposha Oil Industries Co., Ltd.).

Examples of commercial products of the POE fatty acid amide are Nymid MT-215 (produced by NOF Corporation) and Nikkol TAMDS15 (produced by Nikko Chemicals Co., Ltd.).

The polycyclic phenyl in the POE polycyclic phenyl ether sulfuric acid ester salt includes phenyl group substituted with two or more groups (substituents) each having one aromatic ring therein, phenyl group substituted with one or plural groups (substituents) each having two or more aromatic rings therein, etc. Examples of the group having one aromatic ring therein include benzyl and 1-(phenyl)ethyl. An example of a group having two or more aromatic rings therein is naphthyl. Examples of commercial products of the POE polycyclic phenyl ether sulfuric acid ester salt include Newcol 707-SF, Newcol 707-SFC, Newcol 707-SN and Newcol 723-SF (all produced by Nippon Nyukazai Co., Ltd.).

Examples of commercial products of the POE alkylphenyl ether sulfuric acid ester salt include Hitenol N-07, Hitenol N-08 and Hitenol N-17 (all produced by Dai-ichi Kogyo Seiyaku Co., Ltd.).

Examples of commercial products of the POE fatty acid amide sulfuric acid ester salt include Sunamide CF-3 and Sunamide CF-10 (both produced by NOF Corporation).

Examples of commercial products of the POE alkylamine sulfuric acid ester salt include Mignol PA-30 (produced by Ipposha Oil Industries Co., Ltd.).

Examples of commercial products of the N-acyl taurine salt include Nikkol CMT-30 and Nikkol PMT (both produced by Nikko Chemicals Co., Ltd.), and Diapon T paste, Diapon T powder, Diapon K, Diapon LM and Diapon K-MG (all produced by NOF Corporation).

The amino acid in the N-acyl amino acid salt includes sarcosine, alanine, etc. Examples of commercial products of the N-acyl amino acid salt include Sarcosinate LN-30, Sarcosinate CN-30, Sarcosinate LK-30 and Alaninate LN-30 (all produced by Nikko Chemicals Co., Ltd.), and Filet L (produced by NOF Corporation).

Examples of commercial products of the ethylenediamine-POE•POP condensate include Adeka Pluronic TR-701, Adeka Pluronic TR-702, Adeka Pluronic TR-704 and Adeka Pluronic TR-913R (all produced by Adeka Corporation), and Unilube 32TY-65BI (produced by NOF Corporation).

The PPG derivative not including polyethylene glycol therein includes polypropylene glycol (hereinafter abbreviated as PPG), polyoxypropylene alkyl ether (hereinafter abbreviated as POP alkyl ether), etc. As the PPG, PPG having a molecular weight of 1200 or less is preferred. Examples of commercial products of the PPG having a molecular weight of 1200 or less are Uniol D-700 (produced by NOF Corporation) and Newpol PP-400 (produced by Sanyo Chemical Industries, Ltd.). Examples of commercial products of the POP alkyl ether include Unilube MB-2 (produced by NOF Corporation).

Examples of commercial products of the POE-POP condensate represented by general formula (I):

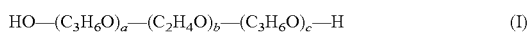

$$\text{HO—}(C_3H_6O)_a\text{—}(C_2H_4O)_b\text{—}(C_3H_6O)_c\text{—H} \tag{I}$$

(wherein a, b and c, which may be the same or different, each represent an integer of 1 to 200) include Pluronic 25R-1 and Pluronic 25R-2 (both produced by Adeka Corporation), and BLAUNON EP-0480, BLAUNON EP-0670 and BLAUNON EP-1461 (all produced by Aoki Oil Industrial Co., Ltd.).

The alkyl in the POE•POP alkyl ether of C9 or less includes methyl, ethyl, propyl, butyl, pentyl, hexyl, heptyl, octyl, nonyl, etc. Examples of commercial products of the POE•POP alkyl ethers of C9 or less include Unilube 50 MB-26 and Unilube 50 MB-72 (both produced by NOF Corporation).

In the present invention, either one kind of surfactant A or a combination of two or more kinds of surfactants A may be used.

On the basis of the disclosure of the present application that there exist surfactants showing an action to inhibit the reaction of cholesterol in sdLDL with cholesterol ester hydrolase and cholesterol oxidase, or cholesterol ester hydrolase, cholesterol dehydrogenase and oxidized coenzyme and to cause a reaction of cholesterol in LgLDL, persons of ordinary skill in the art can easily grasp and select specific examples of surfactant A of the present invention by the following assay, in addition to the above-mentioned ones. The surfactants selected by this method are also included in surfactants A of the present invention.

The determination on surfactant A can be carried out, for example, by the method described below.
1) Separation of Lipoprotein Fractions The fractions of HDL, VLDL, CM, LgLDL and sdLDL in serum are separated and purified according to their specific gravity. Specifically, four lipoprotein fractions of HDL (specific gravity: 1.063 or more), sdLDL (specific gravity: 1.044 to 1.063), LgLDL (specific gravity: 1.006 to 1.044) and VLDL and CM (specific gravity: 1.006 or less) are separated from human serum according to the ultracentrifugation method described in "Shin Seikagaku Jikken Koza 4" (New Lectures on Biochemical Experiments 4) (Tokyo Kagaku Dojin).
2) Reagent for Assessing Suitability for Surfactant A Example 1

Buffer solution, e.g., MOPS (pH 7.0)
Cholesterol ester hydrolase, e.g., LPL3
Cholesterol oxidase, e.g., CHO-PEL
Reagent for measurement of hydrogen peroxide, e.g., peroxidase, N-ethyl-N-(3-methylphenyl)-N'-succinylethylenediamine (EMSE) and 4-aminoantipyrine (4-AA)
Surfactant to be examined

Example 2

Buffer solution, e.g., MOPS (pH 7.0)
Cholesterol ester hydrolase, e.g., LPL3
Cholesterol dehydrogenase, e.g., CHDH5
Oxidized coenzyme, e.g., NAD
[If necessary, reagent for measurement of reduced coenzyme, e.g., 2-(4-iodophenyl)-3-(2,4-dinitrophenyl)-5-(2,4-disulfophenyl)-2H-tetrazolium monosodium salt (WST-3)]
Surfactant to be examined

Example 3

Buffer solution, e.g., MOPS (pH 7.0)
Cholesterol ester hydrolase, e.g., LPL3
Cholesterol dehydrogenase, e.g., CHDH5
Oxidized coenzyme, e.g., NAD
Reduced coenzyme oxidase, e.g., NADH oxidase
Reagent for measurement of hydrogen peroxide, e.g., peroxidase, EMSE and 4-AA
Surfactant to be examined Each of the above reagents may comprise, according to need, an aqueous medium, a stabilizer, an antiseptic, an agent for eliminating affecting substances, a reaction promoter, etc. described below.

3) Method for Assessing Suitability for Surfactant A

Each lipoprotein fraction is added as a sample to a reaction cell (2 μL) and then the reagent described in the above 2) (0.15 mL) is added to initiate the reaction, followed by heating at 37° C. for 5 minutes. The change in absorbance ($\Delta E_{lipoprotein\ fraction}$) of the reaction solution at the time when the absorbance of the reaction solution linearly increases, for example, after 5 minutes of reaction is measured.

A similar measurement is carried out using a physiological saline solution as a sample in place of each lipoprotein fraction and the change in absorbance ($\Delta E_{blank}$) is calculated. "Reaction absorbance 1" for each lipoprotein fraction is calculated according to the following (equation 1).

$$\text{Reaction absorbance 1} = \Delta E_{lipoprotein\ fraction} - \Delta E_{blank} \quad \text{(equation 1)}$$

"Reaction absorbance 2" for each lipoprotein fraction is calculated in a similar manner using Hitachi-7170S autoanalyzer and a kit for determination of total cholesterol, Determiner C TC (Kyowa Medex Co., Ltd.).

Subsequently, the reaction rate for each lipoprotein fraction is calculated according to the following (equation 2).

$$\text{Reactivity (\%)} = \text{Reaction absorbance 1/Reaction absorbance 2} \times 100 \quad \text{(equation 2)}$$

Surfactants giving a low reactivity in the sdLDL fraction and a high reactivity in the LgLDL fraction are selected, and preferably, those giving a low reactivity in the sdLDL fraction and high reactivity in the HDL, VLDL, CM and LgLDL fractions are selected as surfactants A.

The expression "preferentially inhibits a reaction of sdLDL-C with cholesterol ester hydrolase and cholesterol oxidase, or cholesterol ester hydrolase, cholesterol dehydrogenase and oxidized coenzyme compared with the reaction of HDL-C, VLDL-C, CM-C and LgLDL-C with cholesterol ester hydrolase and cholesterol oxidase, or cholesterol ester hydrolase, cholesterol dehydrogenase and oxidized coenzyme" means that the reactivity of cholesterol in the sdLDL fraction is small compared with the reactivity of cholesterol in each of the HDL, VLDL, CM and LgLDL fractions, and the ratio of the reactivity of cholesterol in the sdLDL fraction to the reactivity of cholesterol in each of the HDL, VLDL, CM and LgLDL fractions is preferably 50% or less, more preferably 20% or less, particularly preferably 10% or less.

The reactivity of surfactants may vary according to reaction conditions such as the kind and concentration of the enzymes used, but it is possible to judge whether or not the examined surfactant can be used as surfactant A in the present invention under the given conditions.

The concentration of surfactant A used in the method for determination of sdLDL-C of the present invention is preferably a concentration which enables preferential elimination of cholesterol in lipoproteins other than sdLDL, that is, HDL, VLDL, CM and LgLDL, and its concentration in a reaction solution is preferably 0.0001 to 1%, more preferably 0.0005 to 0.5%.

The reagent which causes a reaction of sdLDL-C in the present invention is a reagent which enables, after the reaction of a sample with cholesterol ester hydrolase and cholesterol oxidase, or cholesterol ester hydrolase, cholesterol dehydrogenase and oxidized coenzyme in the presence of surfactant A to eliminate cholesterol in lipoproteins other than sdLDL, a reaction of sdLDL-C remaining in the reaction solution with cholesterol ester hydrolase and cholesterol oxidase, or cholesterol ester hydrolase, cholesterol dehydrogenase and oxidized coenzyme. Specifically, the reagent includes a surfactant (hereinafter referred to as surfactant B) which releases the inhibition of the reaction of sdLDL-C with cholesterol ester hydrolase and cholesterol oxidase, or cholesterol ester hydrolase, cholesterol dehydrogenase and oxidized coenzyme used for elimination of cholesterol in lipoproteins other than sdLDL in the presence of surfactant A, and an enzyme which enables a reaction with sdLDL-C in the presence of surfactant A.

Examples of surfactant B in the present invention include polyoxyethylene alkyl ether (hereinafter abbreviated as POE alkyl ether), polyoxyethylene polyoxyalkylene alkyl ether (the alkyl is an alkyl having 10 or more carbon atoms) (hereinafter abbreviated as POE•POA alkyl ether of C10 or more), polyoxyethylene alkylphenyl ether (hereinafter abbreviated as POE alkylphenyl ether), polyoxyethylene polyoxyalkylene alkylphenyl ether (hereinafter abbreviated as POE•POA alkylphenyl ether), polyoxyethylene polycyclic phenyl ether (hereinafter abbreviated as POE polycyclic phenyl ether), polyoxyethylene polyoxyalkylene polycyclic phenyl ether (hereinafter abbreviated as POE•POA polycyclic phenyl ether), polyoxyethylene polyoxypropylene condensate represented by general formula (II):

$$HO-(C_2H_4O)_d-(C_3H_6O)_e-(C_2H_4O)_f-H \quad (II)$$

(wherein d, e and f, which may be the same or different, each represent an integer of 1 to 200) (hereinafter abbreviated as POE•POP condensate), and polyoxyethylene polyoxyalkylene alkylamine (hereinafter abbreviated as POE•POA alkylamine).

As the POE alkyl ether, POE alkyl ether with HLB less than 15.0 (the alkyl is alkyl having 20 or less carbon atoms) is preferred. The alkyl in the POE alkyl ether with HLB less than 15.0 (the alkyl is alkyl having 20 or less carbon atoms) includes, for example, methyl, ethyl, propyl, butyl, pentyl, hexyl, heptyl, octyl, nonyl, decyl, isodecyl, undecyl, dodecyl (lauryl), tridecyl, tetradecyl (myristyl), pentadecyl, hexadecyl (cetyl), hexydecyl, heptadecyl, octadecyl (stearyl), nonadecyl, icosyl and octyldodecyl. Examples of commercial products of the POE alkyl ethers with HLB less than 15.0 (the alkyl is alkyl having 20 or less carbon atoms) are Morinol L-80 (HLB 13.1; carbon number 12) (produced by Morin Chemical Industries Co., Ltd), Emulmin NL-80 (HLB 13.1; carbon number 12), Emulmin NL-90 (HLB 13.6; carbon number 12), Emulmin NL-100 (HLB 14.0; carbon number 12) and Emulmin NL-110 (HLB 14.4; carbon number 12) (all produced by Sanyo Chemical Industries, Ltd.), Noigen TDS-80 (HLB 13.3; carbon number 13) and Noigen TDS-120 (HLB 14.8; carbon number 13) (both produced by Dai-ichi Kogyo Seiyaku Co., Ltd.), and EMALEX 1615 (HLB 13.0; carbon number 16), EMALEX 1820 (HLB 14.0; carbon number 18) and EMALEX OD-16 (HLB 12.0; carbon number 20) (all produced by Nihon Emulsion Co., Ltd.).

As the POE•POA alkyl ether of C10 or more, POE•POA alkyl ether with HLB less than 15.0 in which the carbon number of the alkyl is from 10 to 20 are preferred. The alkyl in the POE•POA alkyl ether with HLB less than 15.0 in which the carbon number of the alkyl is from 10 to 20 includes, for example, decyl, isodecyl, undecyl, dodecyl (lauryl), tridecyl, tetradecyl (myristyl), pentadecyl, hexadecyl (cetyl), hexydecyl, heptadecyl, octadecyl (stearyl), nonadecyl, icosyl and octyldodecyl. The polyoxyalkylene in the POE•POA alkyl ether with HLB less than 15.0 in which the carbon number of the alkyl is from 10 to 20 includes polyoxyalkylene other than polyoxyethylene, such as polyoxypropylene and polyoxybutylene. Examples of commercial products of the POE•POA alkyl ether with HLB less than 15.0 in which the carbon number of the alkyl is from 10 to 20 are Wondersurf ID-50 (HLB 10.5; carbon number 10), Wondersurf ID-70 (HLB 12.1; carbon number 10), Wondersurf ID-90 (HLB 13.3; carbon number 10), Wondersurf S-800 (HLB 12.3; carbon number 13), Wondersurf S-1000 (HLB 13.2; carbon number 13) and Wondersurf S-1400 (HLB 14.4; carbon number 13) (all produced by Aoki Oil Industrial Co., Ltd.).

As the POE alkylphenyl ether, POE alkylphenyl ether with HLB less than 16.0 is preferred. The alkyl in the POE alkylphenyl ether with HLB less than 16.0 includes alkyl group having 1 to 30 carbon atoms, such as methyl, ethyl, propyl, butyl, pentyl, hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl and triacontyl. Examples of commercial products of the POE alkylphenyl ethers with HLB less than 16.0 are Nonion NS-210 (HLB 13.3), Nonion NS-212 (HLB 14.1), Nonion NS-215 (HLB 15.0) and Nonion NS-210 (HLB 13.6) (all produced by NOF Corporation), and Emulgen 911 (HLB 13.7) and Emulgen 913 (HLB 14.5) (both produced by Kao Corporation).

As the POE•POA alkylphenyl ether, POE•POA alkylphenyl ether with HLB less than 16.0 is preferred. The alkyl in the POE•POA alkylphenyl ether with HLB less than 16.0 includes alkyl groups having 1 to 30 carbon atoms, such as methyl, ethyl, propyl, butyl, pentyl, hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl and triacontyl. The polyoxyalkylene in the POE•POA alkylphenyl ether with HLB less than 16.0 includes polyoxyalkylenes other than polyoxyethylene, such as polyoxypropylene and polyoxybutylene. Examples of commercial products of the POE•POA alkylphenyl ether with HLB less than 16.0 include Acronecess KP-189R and Dispanol LS-100 (both produced by NOF Corporation) and Emulgen L-40 (produced by Kao Corporation).

As the POE polycyclic phenyl ether, POE polycyclic phenyl ether with HLB less than 13.0 is preferred. The polycyclic phenyl in the POE polycyclic phenyl ether with HLB less than 13.0 includes phenyl group substituted with two or more groups (substituents) each having one aromatic ring therein, phenyl group substituted with one or plural groups (substituents) each having two or more aromatic rings therein, etc. Examples of a group having one aromatic ring therein include benzyl and 1-(phenyl)ethyl. Examples of the group having two or more aromatic rings therein include naphthyl. Examples of commercial products of the POE polycyclic phenyl ethers with HLB less than 13.0 are Emulgen A-60 (HLB 12.8) (produced by Kao Corporation), BLAUNON DSP-9 (HLB 11.4) and BLAUNON DSP-12.5 (HLB 12.8) (both produced by Aoki Oil Industrial Co., Ltd.), and Newcol 2607 (HLB 11.8) (produced by Nippon Nyukazai Co., Ltd.).

As the POE•POA polycyclic phenyl ether, POE•POA polycyclic phenyl ether with HLB less than 13.0 is preferred. The polycyclic phenyl in the POE•POA polycyclic phenyl ether with HLB less than 13.0 includes phenyl group substituted with two or more groups (substituents) each having one aromatic ring therein, phenyl group substituted with one or plural groups (substituents) each having two or more aromatic rings therein, etc. Examples of a group having one aromatic ring therein include benzyl and 1-(phenyl)ethyl. Examples of a group having two or more aromatic rings therein include naphthyl. The polyoxyalkylene in the POE•POA polycyclic phenyl ether with HLB less than 13.0 includes polyoxyalkylene other than polyoxyethylene, such as polyoxypropylene and polyoxybutylene. Examples of commercial products of the POE•POA polycyclic phenyl ether with HLB less than 13.0 include Newcol 707F (HLB 12.4) (produced by Nippon Nyukazai Co., Ltd.).

As the POE•POP condensate represented by general formula (II):

$$HO-(C_2H_4O)_d-(C_3H_6O)_e-(C_2H_4O)_f-H \quad (II)$$

(wherein d, e and f, which may be the same or different, each represent an integer of 1 to 200), POE•POP condensate having a POP molecular weight of 1200 or more and a POE content of 60% or less is preferred. Examples of commercial products of the POE•POP condensate having a POP molecular weight of 1200 or more and a POE content of 60% or less include Pronon 204 (POP molecular weight: 2000; POE content: 40%) (produced by NOF Corporation), Newpol PE-62 (POP molecular weight: 1750; POE content: 20%), Newpol PE-64 (POP molecular weight: 1750; POE content: 40%), Newpol PE-71 (POP molecular weight: 2050; POE content: 10%) and Newpol PE-75 (POP molecular weight: 2050; POE content: 50%) (all produced by Sanyo Chemical Industries, Ltd.), and Pluronic P-84 (POP molecular weight: 2250; POE content: 40%), Pluronic P-85 (POP molecular weight: 2250; POE content: 50%) and Pluronic P-103 (POP molecular weight: 3250; POE content: 30%) (all produced by Adeka Corporation).

The alkyl in the POE•POA alkylamine includes alkyl group having 1 to 30 carbon atoms, such as methyl, ethyl, propyl, butyl, pentyl, hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl and triacontyl. The polyoxyalkylene in the POE•POA alkylamine includes polyoxyalkylenes other than polyoxyethylene, such as polyoxypropylene and polyoxybutylene. Examples of commercial products of the POE•POA alkylamine include BLAUNON LPE1007 (produced by Aoki Oil Industrial Co., Ltd.) and Alkyl(C16)amine EO20PO10 (produced by NOF Corporation).

In the present invention, either one kind of surfactant B or a combination of two or more kinds of surfactants B may be used.

Persons of ordinary skill in the art can appropriately grasp and select surfactant which increases the reactivity of sdLDL fraction as surfactants B by the method shown in Example 2 of the present invention or the like. The reactivity of surfactants may vary according to the difference of reaction conditions such as the kind and concentration of the enzymes used, but it is possible to judge whether or not the examined surfactant can be used as surfactant B in the present invention under the given conditions.

The concentration of surfactant B used in the method for determination of sdLDL-C of the present invention is a concentration which enables determination of sdLDL-C, and its concentration in a reaction solution is preferably 0.001 to 5%, more preferably 0.01 to 0.5%.

Examples of the enzyme which enables the reaction with sdLDL-C in the presence of surfactant A include cholesterol ester hydrolase, cholesterol oxidase and cholesterol dehydrogenase, among which cholesterol ester hydrolase is preferred. When cholesterol ester hydrolase is used in place of surfactant B, the cholesterol ester hydrolase used may be of the same kind as the cholesterol ester hydrolase used in step (i) or may be of a different kind. When cholesterol ester hydrolase of the same kind is used, the cholesterol ester hydrolase is added in an amount enabling the determination of the remaining sdLDL-C in step (ii). When cholesterol ester hydrolase of a different kind is used, there is no specific restriction as long as it is cholesterol ester hydrolase which enables the determination of the remaining sdLDL-C.

In step (ii), a combination of an enzyme and a surfactant can also be used as the reagent which causes the reaction of sdLDL-C. There is no specific restriction as to the combination, as long as it is a combination which enables the determination of sdLDL-C remaining in the reaction solution after the elimination of lipoproteins other than sdLDL. It is not necessary that each of the enzyme and surfactant constituting the combination should enable the determination of the remaining sdLDL-C when used singly, and it is sufficient that their combined use can enable the determination of the remaining sdLDL-C.

The HLB refers to hydrophile-lipophile balance value. The HLB of a surfactant used in the present invention, for example, that of POE polycyclic phenyl ether can be calculated by the methods described in "Surfactant Handbook" (Tokiyuki Yoshida, et al., Kogyo Tosho Co., Ltd.) and "New Surfactants" (Hiroshi Horiguchi, Sankyo Publishing Co., Ltd.). It is also possible to refer to HLB values described in catalogues and pamphlets released from manufacturers of various kinds of surfactants.

(Method for Determination of sdLDL-C)

The method for determination of sdLDL-C of the present invention is a method comprising the following steps (i) to (iii).

(i) a step of allowing cholesterol ester hydrolase and cholesterol oxidase, or cholesterol ester hydrolase, cholesterol dehydrogenase and oxidized coenzyme to act on a sample in a reaction solution containing surfactant A to eliminate cholesterol in lipoproteins other than sdLDL in the sample (ii) a step of adding a reagent which causes a reaction of sdLDL-C remaining in the reaction solution after the above step (i) to form hydrogen peroxide or reduced coenzyme, and measuring the formed hydrogen peroxide or reduced coenzyme (iii) a step of carrying out the above steps (i) and (ii) using standard samples containing known concentrations of sdLDL-C to form hydrogen peroxide or reduced coenzyme, measuring the formed hydrogen peroxide or reduced coenzyme, correlating the sdLDL-C concentration with the measurement value on hydrogen peroxide or reduced coenzyme, and determining the sdLDL-C concentration in the sample The method for detecting sdLDL-C in a sample may also be performed by carrying out step (i) and step (ii) without carrying out step (iii).

An example of the method for eliminating cholesterol in lipoproteins other than sdLDL in a sample in step (i) is a method of eliminating hydrogen peroxide converted from the cholesterol or reduced coenzyme formed from the cholesterol. As the elimination method, a method which comprises forming hydrogen peroxide from the cholesterol and then eliminating the hydrogen peroxide is preferred.

Elimination of hydrogen peroxide can be carried out, for example, by using a reagent for eliminating hydrogen peroxide. Preferred methods for eliminating hydrogen peroxide are a method in which hydrogen peroxide is acted on catalase and a method in which hydrogen peroxide is acted on a combination of a peroxidative substance and one part of the two oxidative coupling-type chromogens used for oxidative coupling coloring reaction.

Elimination of reduced coenzyme can be carried out, for example, by allowing reduced coenzyme oxidase to act on reduced coenzyme and eliminating the formed hydrogen peroxide by using a reagent for eliminating hydrogen peroxide.

There is no specific restriction as to the reagent for eliminating hydrogen peroxide, as long as it is a reagent converting hydrogen peroxide formed from lipoprotein cholesterol other than sdLDL-C into a substance which does not affect the measurement of hydrogen peroxide formed from sdLDL-C, and examples of the reagent are a reagent comprising catalase and a reagent comprising a peroxidative substance and one part of the two oxidative coupling-type chromogens used for oxidative coupling coloring reaction. An example of the peroxidative substance is peroxidase. Specific examples of the one part of the two oxidative coupling-type chromogens used for oxidative coupling coloring reaction are a coupler and an aniline compound or a phenol compound in oxidative coupling-type chromogens described below. In the present specification, the term "the other part of oxidative coupling-type chromogen" is used in pair with the term "one part of the two oxidative coupling-type chromogens used for oxidative coupling coloring reaction". For example, when the former refers to a coupler, the latter refers to a phenol compound or an aniline compound, and when the former refers to a phenol compound or an aniline compound, the latter refers to a coupler.

When a reagent comprising catalase is used as the reagent for eliminating hydrogen peroxide, the concentration of catalase is preferably 0.001 to 5000 kU/L, more preferably 0.01 to 1000 kU/L. When catalase is used as the reagent for eliminating hydrogen peroxide in step (i) of the present invention, it is preferred to allow a catalase inhibitor to be present in step (ii). Examples of the catalase inhibitor include sodium azide, $H_2S$, HCN, $NH_2OH$ and 3-amino-1,2,4-triazole. There is no specific restriction as to the concentration of the catalase inhibitor to be used as long as it is a concentration which inhibits catalase activity and which does not affect the measurement of hydrogen peroxide formed in step (ii), and its concentration is preferably 0.5 to 60 mmol/L, more preferably 1 to 30 mmol/L.

When a peroxidative substance and one part of the two oxidative coupling-type chromogens used for oxidative coupling coloring reaction are used as the reagent for eliminating hydrogen peroxide, peroxidase or the like is used as the peroxidative substance. The concentration of peroxidase is preferably 0.01 to 500 kU/L, more preferably 1 to 100 kU/L, and the concentration of one part of the two oxidative coupling-type chromogens used for oxidative coupling coloring reaction is preferably 0.01 to 10 g/L.

In the present invention, the elimination of cholesterol in lipoproteins other than sdLDL in step (i) is not limited to the elimination by conversion of hydrogen peroxide or reduced coenzyme formed from the cholesterol into another substance. For instance, when hydrogen peroxide and reduced coenzyme can be measured separately, hydrogen peroxide or reduced coenzyme formed from the cholesterol is not required to be converted into another substance. For example, when reduced coenzyme is formed from cholesterol in lipoproteins other than sdLDL in step (i) and hydrogen peroxide is formed from cholesterol in sdLDL in step (ii), the reduced coenzyme formed in step (i) does not need to be converted into another substance. Further, the present invention includes the determination of sdLDL-C in a sample by calculating the amount of hydrogen peroxide or reduced coenzyme formed in step (ii) based on the measurement value obtained by measuring hydrogen peroxide or reduced coenzyme formed in step (i).

The measurement of hydrogen peroxide can be carried out, for example, by using a hydrogen peroxide electrode or a reagent for measuring hydrogen peroxide described below. Preferred is a method which comprises allowing the peroxidative substance and the oxidative coloring-type chromogen to act on hydrogen peroxide to form a dye and measuring the absorbance of the dye.

The measurement of reduced coenzyme can be carried out, for example, by the measurement of absorbance at a wavelength around the absorption maximum of reduced coenzyme or the measurement using a reagent for measuring reduced coenzyme described below.

The reagent for measuring hydrogen peroxide is a reagent for converting the formed hydrogen peroxide into a detectable substance. Examples of the detectable substance include a dye and luminescence, and preferred is a dye. When the detectable substance is a dye, the reagent for measuring hydrogen peroxide comprises the oxidative coloring type chromogen and the peroxidative substance such as peroxidase. Examples of the oxidative coloring type chromogen include oxidative coloring type chromogens described below. When the detectable substance is luminescence, the reagent for measuring hydrogen peroxide comprises a chemiluminescent substance. Examples of the chemiluminescent substance include luminol, isoluminol, lucigenin and acridinium ester.

When a reagent comprising an oxidative coloring type chromogen and a peroxidative substance is used as the reagent for measuring hydrogen peroxide, hydrogen peroxide can be measured by subjecting hydrogen peroxide to reaction with the oxidative coloring type chromogen in the presence of the peroxidative substance to form a dye and measuring the formed dye. When a reagent for measuring hydrogen peroxide comprising a chemiluminescent substance is used, hydrogen peroxide can be measured by subjecting hydrogen peroxide to reaction with the chemiluminescent substance to generate luminescence and measuring the generated luminescence.

Examples of the oxidative coloring type chromogen are leuco-type chromogens and oxidative coupling-type chromogens.

The leuco-type chromogen is a substance that is converted into a dye by itself in the presence of hydrogen peroxide and a peroxidative substance. Examples of the leuco-type chromogen include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 4,4'-bis(dimethylamino)diphenylamine and bis[3-bis(4-chlorophenyl)methyl-4-dimethylaminophenyl]amine (BCMA).

The oxidative coupling-type chromogen is a substance that forms a dye by an oxidative coupling of two compounds in the presence of hydrogen peroxide and a peroxidative substance. Examples of the combinations of the two compounds include a combination of a coupler and an aniline compound and a combination of a coupler and a phenol compound.

Examples of the coupler include 4-aminoantipyrine (4-AA) and 3-methyl-2-benzothiazolinone hydrazine.

Examples of the aniline compound include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-bis(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxylaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine and N-ethyl-N-(2-hydroxy-3-sulfopropyl)-4-fluoro-3,5-dimethoxyaniline (F-DAOS).

Examples of the phenol compound include phenol, 4-chlorophenol, 3-methylphenol and 3-hydroxy-2,4,6-triuodobenzoic acid (HTIB).

The reagent for measuring reduced coenzyme is a reagent for converting the formed reduced coenzyme into a detectable substance. Examples of the detectable substance include a dye. When the detectable substance is a dye, the reagent for measuring reduced coenzyme comprises a reductive coloring type chromogen. Examples of the reductive coloring type chromogen include 3-(4,5-dimethyl-2-thiazolyl)-2,5-diphenyl-2H-tetrazolium bromide (MTT), 2-(4-iodophenyl)-3-(4-nitrophenyl)-5-(2,4-disulfophenyl)-2H-tetrazolium monosodium salt (WST-1) and 2-(4-iodophenyl)-3-(2,4-dinitrophenyl)-5-(2,4-disulfophenyl)-2H-tetrazolium monosodium salt (WST-3).

In the measurement of hydrogen peroxide, peroxidase or the like is used as the peroxidative substance. The concentration of a peroxidative substance is not specifically restricted as long as it is suited for the measurement. When peroxidase is used as the peroxidative substance, its concentration is preferably 1 to 100 kU/L. The concentration of an oxidative coloring type chromogen is not specifically restricted as long as it is suited for the measurement, and it is preferably 0.01 to 10 g/L.

In the present invention, it is preferred that the measurement of sdLDL-C is carried out in an aqueous medium. Examples of the aqueous medium include deionized water, distilled water and a buffer solution, and preferred is a buffer solution. Examples of the buffer used in the buffer solution are tris(hydroxymethyl)aminomethane buffer, phosphate buffer, borate buffer and Good's buffer.

Examples of Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO) and N-cyclohexyl-3-aminopropanesulfonic acid (CAPS). The concentration of the buffer solution is not specifically restricted as long as it is suited for the measurement, but it is preferably 0.001 to 2.0 mol/L, more preferably 0.005 to 1.0 mol/L.

A calibration curve used for determining the sdLDL-C concentration in a sample can be prepared, for example, by carrying out step (i) and step (ii) of the present invention using standard samples with known concentrations of sdLDL-C to form hydrogen peroxide or reduced coenzyme, measuring the formed hydrogen peroxide or reduced coenzyme, and preparing the curve from the measurement values and the used sdLDL-C concentrations.

Step (i) and step (ii) of the present invention are carried out, for example, at 10 to 50° C., preferably 20 to 40° C. for 1 to 30 minutes, preferably 2 to 15 minutes.

(Kit for Determination of sdLDL-C)

The kit for determination of sdLDL-C of the present invention can be used in the method for determination of sdLDL-C of the present invention. There is no specific restriction as to the form of the kit for determination of sdLDL-C as long as the method for determination of sdLDL-C of the present invention can be performed. The kit may be composed of two reagents or three reagents, and preferred is the kit composed of two reagents.

Examples of the kit for determination of sdLDL-C of the present invention are shown below.

The kit for determination of sdLDL-C in a sample, which comprises a first reagent comprising surfactant A, cholesterol ester hydrolase, cholesterol oxidase and a reagent for eliminating hydrogen peroxide, and a second reagent comprising a reagent which causes the reaction of sdLDL-C and a reagent for measuring hydrogen peroxide.

The kit for determination of sdLDL-C in a sample, which comprises a first reagent comprising surfactant A, cholesterol ester hydrolase, oxidized coenzyme and cholesterol dehydrogenase, and a second reagent comprising a reagent which causes the reaction of sdLDL-C.

The kit for determination of sdLDL-C, which comprises a first reagent comprising surfactant A, cholesterol ester hydrolase, oxidized coenzyme, cholesterol dehydrogenase and a reagent for measuring reduced coenzyme, and a second reagent comprising a reagent which causes the reaction of sdLDL-C.

The kit for determination of sdLDL-C in a sample, which comprises a first reagent comprising surfactant A, cholesterol ester hydrolase, cholesterol dehydrogenase, oxidized coenzyme, reduced coenzyme oxidase and a reagent for eliminating hydrogen peroxide, and a second reagent comprising a reagent which causes the reaction of sdLDL-C and a reagent for measuring hydrogen peroxide.

The kit for determination of sdLDL-C, which comprises a first reagent comprising surfactant A, cholesterol ester hydrolase, cholesterol oxidase and a reagent for eliminating hydrogen peroxide, and a second reagent comprising surfactant B and a reagent for measuring hydrogen peroxide.

The kit for determination of sdLDL-C, which comprises a first reagent comprising surfactant A, cholesterol ester hydrolase, oxidized coenzyme and cholesterol dehydrogenase, and a second reagent comprising surfactant B.

The kit for determination of sdLDL-C, which comprises a first reagent comprising surfactant A, cholesterol ester hydrolase, oxidized coenzyme, cholesterol dehydrogenase and a reagent for measuring reduced coenzyme, and a second reagent comprising surfactant B.

The kit for determination of sdLDL-C, which comprises a first reagent comprising surfactant A, cholesterol ester hydrolase, oxidized coenzyme, cholesterol dehydrogenase, reduced coenzyme oxidase and a reagent for eliminating hydrogen peroxide, and a second reagent comprising surfactant B and a reagent for measuring hydrogen peroxide.

In the kit for the determination of sdLDL-C composed of two reagents (a first reagent and a second reagent), cholesterol ester hydrolase is contained in the first reagent, and may be contained in both of the first reagent and the second reagent. Cholesterol oxidase is contained in the first reagent, and may be contained in both of the first reagent and the second reagent. Cholesterol dehydrogenase is contained in the first reagent, and may be contained in both of the first reagent and the second reagent.

Surfactant A is preferably contained in the first reagent.

Oxidized coenzyme is contained in the first reagent, and may be contained in both of the first reagent and the second reagent. Reduced coenzyme oxidase is contained in the first reagent, and may be contained in both of the first reagent and the second reagent.

A reagent for eliminating hydrogen peroxide is preferably contained in the first reagent. When catalase is used as the reagent for eliminating hydrogen peroxide, catalase is preferably contained in the first reagent and a catalase inhibitor is preferably contained in the second reagent. When a combination of peroxidase and one part of the two oxidative coupling-type chromogens used for oxidative coupling coloring reaction is used as the reagent for eliminating hydrogen peroxide, said combination is preferably contained in the first reagent.

Surfactant B is preferably contained in the second reagent. As described above, an enzyme which enables the determination of sdLDL-C remaining in the reaction solution after the elimination of cholesterol in lipoproteins other than sdLDL can be used alone or in combination with a surfactant, in place of surfactant B.

When a reagent comprising peroxidase and two oxidative coupling-type chromogens is used as the reagent for measuring hydrogen peroxide, each of the two oxidative coupling-type chromogens is preferably contained in each reagent. Peroxidase may be contained in either or both of the first reagent and the second reagent. When a combination of peroxidase and one part of the two oxidative coupling-type chromogens used for oxidative coupling coloring reaction is used as the reagent for eliminating hydrogen peroxide, said combination may be further combined with the other coupling-type chromogen to serve as the reagent for measuring hydrogen peroxide. The other part of coupling-type chromogen is contained in the second reagent.

Albumin is preferably contained in the first reagent, and may be contained in both of the first reagent and the second reagent.

Certain embodiments of the kit for the determination of sdLDL-C of the present invention are illustrated below, but they are not to be construed as limiting the scope of the present invention.

Kit 1
First Reagent
 Surfactant A, cholesterol ester hydrolase, cholesterol oxidase and catalase
Second Reagent
 Surfactant B, a catalase inhibitor and a reagent for measuring hydrogen peroxide Kit 2
First Reagent
 Surfactant A, cholesterol ester hydrolase, cholesterol oxidase, peroxidase and one part of the two oxidative coupling-type chromogens
Second Reagent
 Surfactant B and the other part of oxidative coupling-type chromogen Kit 3
First Reagent
 Surfactant A, cholesterol ester hydrolase, cholesterol oxidase, peroxidase and oxidative coupling-type chromogens
Second Reagent
 Surfactant B Kit 4
First Reagent
 Surfactant A, cholesterol ester hydrolase, oxidized coenzyme and cholesterol dehydrogenase
Second Reagent
 Surfactant B Kit 5
First Reagent
 Surfactant A, cholesterol ester hydrolase, oxidized coenzyme, cholesterol dehydrogenase and a reagent for measuring reduced coenzyme
Second Reagent
 Surfactant B Kit 6
First Reagent
 Surfactant A, cholesterol ester hydrolase, oxidized coenzyme, cholesterol dehydrogenase, reduced coenzyme oxidase and catalase
Second Reagent
 Surfactant B, a catalase inhibitor and a reagent for measuring hydrogen peroxide Kit 7
First Reagent
 Surfactant A, cholesterol ester hydrolase, oxidized coenzyme, cholesterol dehydrogenase, reduced coenzyme oxidase, peroxidase and one part of the two oxidative coupling-type chromogens
Second Reagent
 Surfactant B and the other part of oxidative coupling-type chromogen Kit 8
First Reagent
 Surfactant A, cholesterol ester hydrolase, cholesterol oxidase, catalase and albumin
Second Reagent
 Surfactant B, a catalase inhibitor and a reagent for measuring hydrogen peroxide Kit 9
First Reagent
 Surfactant A, cholesterol ester hydrolase, cholesterol oxidase, peroxidase, one part of the two oxidative coupling-type chromogens and albumin
Second Reagent
 Surfactant B and the other part of oxidative coupling-type chromogen Kit 10
First Reagent
 Surfactant A, cholesterol ester hydrolase, cholesterol oxidase, peroxidase, oxidative coupling-type chromogens and albumin
Second Reagent
 Surfactant B Kit 11
First Reagent
 Surfactant A, cholesterol ester hydrolase, oxidized coenzyme, cholesterol dehydrogenase and albumin
Second Reagent
 Surfactant B Kit 12
First Reagent
 Surfactant A, cholesterol ester hydrolase, oxidized coenzyme, cholesterol dehydrogenase, a reagent for measuring reduced coenzyme and albumin
Second Reagent
 Surfactant B Kit 13
First Reagent
 Surfactant A, cholesterol ester hydrolase, oxidized coenzyme, cholesterol dehydrogenase, reduced coenzyme oxidase, catalase and albumin
Second Reagent
 Surfactant B, a catalase inhibitor and a reagent for measuring hydrogen peroxide Kit 14
First Reagent
 Surfactant A, cholesterol ester hydrolase, oxidized coenzyme, cholesterol dehydrogenase, reduced coenzyme oxidase, peroxidase, one part of the two oxidative coupling-type chromogens and albumin
Second Reagent
 Surfactant B and the other part of oxidative coupling-type chromogen Kit 15
First Reagent
 Surfactant A, cholesterol ester hydrolase, cholesterol oxidase, catalase and albumin
Second Reagent
 Surfactant B, a catalase inhibitor, a reagent for measuring hydrogen peroxide and albumin Kit 16
First Reagent
 Surfactant A, cholesterol ester hydrolase, cholesterol oxidase, peroxidase, one part of the two oxidative coupling-type chromogens and albumin
Second Reagent
 Surfactant B, albumin and the other part of oxidative coupling-type chromogen Kit 17
First Reagent
 Surfactant A, cholesterol ester hydrolase, cholesterol oxidase, peroxidase, oxidative coupling-type chromogens and albumin
Second Reagent
 Surfactant B and albumin Kit 18
First Reagent
  Surfactant A, cholesterol ester hydrolase, oxidized coenzyme, cholesterol dehydrogenase and albumin
Second Reagent
  Surfactant B and albumin
Kit 19
First Reagent
  Surfactant A, cholesterol ester hydrolase, oxidized coenzyme, cholesterol dehydrogenase, a reagent for measuring reduced coenzyme and albumin
Second Reagent
  Surfactant B and albumin
Kit 20
First Reagent
  Surfactant A, cholesterol ester hydrolase, oxidized coenzyme, cholesterol dehydrogenase, reduced coenzyme oxidase, catalase and albumin
Second Reagent
  Surfactant B, a catalase inhibitor, a reagent for measuring hydrogen peroxide and albumin
Kit 21
First Reagent
  Surfactant A, cholesterol ester hydrolase, oxidized coenzyme, cholesterol dehydrogenase, reduced coenzyme oxidase, peroxidase, one part of the two oxidative coupling-type chromogens and albumin
Second Reagent
  Surfactant B, albumin and the other part of oxidative coupling-type chromogen As the following substances used in the kit for determination of sdLDL-C of the present invention, those described above are exemplified: surfactant A, cholesterol ester hydrolase, cholesterol oxidase, oxidized coenzyme, cholesterol dehydrogenase, reduced coenzyme oxidase, a reagent for eliminating hydrogen peroxide, surfactant B, albumin and a reagent for measuring hydrogen peroxide.

The kit for determination of sdLDL-C of the present invention may comprise, according to need, an aqueous medium, a stabilizer, an antiseptic, an agent for eliminating affecting substances, a reaction promoter, etc. Examples of the aqueous medium include the above-mentioned aqueous media. Examples of the stabilizer include ethylenediaminetetraacetic acid (EDTA), sucrose and calcium chloride. Examples of the antiseptic include sodium azide, Bioace and an antibiotic. Examples of the agent for eliminating affecting substances include ascorbate oxidase to inhibit the effect of ascorbic acid. Examples of the reaction promoter include enzymes such as colipase, and salts such as sodium sulfate and sodium chloride.

The kit for determination of sdLDL-C of the present invention may be in freeze-dried form or in a state of being dissolved in an aqueous medium. When sdLDL-C in a sample is determined using a reagent in freeze-dried form, the reagent is used after being dissolved in an aqueous medium.

Cholesterol ester hydrolase and cholesterol oxidase are contained in the kit for determination of sdLDL-C of the present invention in such amount that the concentration thereof when dissolved in an aqueous medium becomes preferably 0.001 to 2000 U/mL, more preferably 0.005 to 1000 U/mL.

Cholesterol dehydrogenase and reduced coenzyme oxidase contained in the kit for determination of sdLDL-C of the present invention in such amount that the concentration thereof when dissolved in an aqueous medium becomes preferably 0.001 to 2000 U/mL, more preferably 0.005 to 1000 U/mL.

Oxidized coenzyme is contained in the kit for determination of sdLDL-C of the present invention in such amount that the concentration thereof when dissolved in an aqueous medium becomes preferably 0.01 to 500 mmol/L, more preferably 0.1 to 100 mmol/L.

Surfactant A is contained in the kit for determination of sdLDL-C of the present invention in such amount that the concentration thereof when dissolved in an aqueous medium becomes preferably 0.0001 to 1%, more preferably 0.0005 to 0.5%.

Surfactant B is contained in the kit for determination of sdLDL-C of the present invention in such amount that the concentration thereof in an aqueous medium becomes preferably 0.001 to 5%, more preferably 0.01 to 0.5%.

Albumin is contained in the kit for determination of sdLDL-C of the present invention in such amount that the concentration thereof when dissolved in an aqueous medium becomes preferably 0.0001 to 10%, more preferably 0.001 to 5%.

The present invention is described in more detail by referring to the following examples, which are not to be construed as limiting the scope of the present invention. In the examples and reference examples, reagents and enzymes produced by the following manufacturers were used.

MOPS (Dojindo Laboratories), EMSE (Daito Chemix Corporation), sodium sulfate (Kanto Chemical Co., Inc.), 4-aminoantipyrine (Saikyo Kasei Co., Ltd.), peroxidase (Toyobo Co., Ltd.), CHO-PEL (cholesterol oxidase; Kikkoman Corporation), CHO-CE (cholesterol oxidase; Kikkoman Corporation), COO-322 (cholesterol oxidase; Toyobo Co., Ltd.), LPL3 (cholesterol esterase; Amano Enzyme Inc.), LP (cholesterol esterase; Asahi Kasei Corporation), LIPS (cholesterol esterase; Asahi Kasei Corporation), LPAP (cholesterol esterase; Asahi Kasei Corporation), peroxidase (Toyobo Co., Ltd.) and BSA (Proliant Inc.)

Pionin D-3110 (Takemoto Oil and Fat Co., Ltd.), Pionin D-3120 (Takemoto Oil and Fat Co., Ltd.), Nymeen L-207 (NOF Corporation), Unisafe AL-E (NOF Corporation), ZWITTERGENT 3-10 (CALBIOCHEM), Nissan Anon BL (NOF Corporation), Anon BDF-SF (NOF Corporation), Bisnol SK (Ipposha Oil Industries Co., Ltd.), Nymid MT-215 (NOF Corporation), Newcol 707-SF (Nippon Nyukazai Co., Ltd.), Newcol 723-SF (Nippon Nyukazai Co., Ltd.), Hitenol N-17 (Dai-ichi Kogyo Seiyaku Co., Ltd.), Sunamide CF-10 (NOF Corporation), Mignol PA-30 (Ipposha Oil Industries Co., Ltd.), Nikkol CMT-30 (Nikko Chemicals Co., Ltd.), Sarcosinate LN-30 (Nikko Chemicals Co., Ltd.), Adeka Pluronic TR-704 (Adeka Corporation), Uniol D-700 (NOF Corporation), Pluronic 25R-2 (Adeka Corporation) and Unilube 50 MB-26 (NOF Corporation).

Noigen TDS-80 (Dai-ichi Kogyo Seiyaku Co., Ltd.), Noigen TDS-120 (Dai-ichi Kogyo Seiyaku Co., Ltd.), EMALEX OD-16 (Nihon Emulsion Co., Ltd.), Wondersurf S-800 (Aoki Oil Industrial Co., Ltd.), Wondersurf S-1400 (Aoki Oil Industrial Co., Ltd.), Nonion NS-210 (NOF Corporation), Nonion NS-215 (NOF Corporation), Newcol 2607 (Nippon Nyukazai Co., Ltd.), Emulgen A-60 (Kao Corporation), BLAUNON DSP-12.5 (Aoki Oil Industrial Co., Ltd.), Newpol PE-64 (Sanyo Chemical Industries, Ltd.) and BLAUNON LPE1007 (Aoki Oil Industrial Co., Ltd.)

Example 1

Kits for determination of sdLDL-C comprising the following first reagent and second reagent were prepared. The kits prepared using surfactants A and surfactants B shown in Table 1 were designated as kits of Example 1(1) to 1(34), respectively.

First reagent

| | |
|---|---|
| MOPS (pH 7.0) | 20 mmol/L |
| EMSE | 0.3 g/L |
| Sodium sulfate | 2 g/L |
| Surfactant A (hereinafter abbreviated as "sur. A") | |
| LPL3 | 100 kU/L |
| CHO-PEL | 1 kU/L |
| Peroxidase | 10 kU/L |

Second reagent

| | |
|---|---|
| MOPS (pH 7.0) | 20 mmol/L |
| 4-Aminoantipyrine | 0.3 g/L |
| Peroxidase | 20 kU/L |
| Surfactant B (hereinafter abbreviated as "sur. B") | |

TABLE 1

| # | | Surfactant | Concentration (g/L) |
|---|---|---|---|
| (1) | sur. A | Pionin D-3110 | 0.01 |
| | sur. B | BLAUNON LPE1007 | 1 |
| | | Wondersurf S-800 | 0.3 |
| (2) | sur. A | Pionin D-3110 | 0.01 |
| | | Adeka Pluronic TR-704 | 0.1 |
| | sur. B | BLAUNON LPE1007 | 1 |
| | | Wondersurf S-800 | 0.3 |
| (3) | sur. A | Pionin D-3120 | 0.06 |
| | sur. B | BLAUNON LPE1007 | 1 |
| | | Wondersurf S-800 | 0.3 |
| (4) | sur. A | Unisafe A-LE | 0.06 |
| | sur. B | BLAUNON LPE1007 | 1 |
| | | Wondersurf S-800 | 0.3 |
| (5) | sur. A | ZWITTERGENT 3-10 | 0.1 |
| | sur. B | BLAUNON LPE1007 | 1 |
| | | Wondersurf S-800 | 0.3 |
| (6) | sur. A | Nissan Anon BL | 0.3 |
| | sur. B | BLAUNON LPE1007 | 1 |
| | | Wondersurf S-800 | 0.3 |
| (7) | sur. A | Anon BDF-SF | 0.03 |
| | sur. B | BLAUNON LPE1007 | 1 |
| | | Wondersurf S-800 | 0.3 |
| (8) | sur. A | Bisnol SK | 0.005 |
| | sur. B | BLAUNON LPE1007 | 1 |
| | | Wondersurf S-800 | 0.3 |
| (9) | sur. A | Nymid MT-215 | 0.005 |
| | sur. B | BLAUNON LPE1007 | 1 |
| | | Wondersurf S-800 | 0.3 |
| (10) | sur. A | Newcol 723-SF | 0.1 |
| | sur. B | BLAUNON LPE1007 | 1 |
| | | Wondersurf S-800 | 0.3 |
| (11) | sur. A | Hitenol N-17 | 0.06 |
| | sur. B | BLAUNON LPE1007 | 1 |
| | | Wondersurf S-800 | 0.3 |
| (12) | sur. A | Sunamide CF-10 | 0.1 |
| | sur. B | BLAUNON LPE1007 | 1 |
| | | Wondersurf S-800 | 0.3 |
| (13) | sur. A | Mignol PA-30 | 0.03 |
| | sur. B | BLAUNON LPE1007 | 1 |
| | | Wondersurf S-800 | 0.3 |
| (14) | sur. A | Nikkol CMT-30 | 0.03 |
| | sur. B | BLAUNON LPE1007 | 1 |
| | | Wondersurf S-800 | 0.3 |
| (15) | sur. A | Sarcosinate LN-30 | 0.06 |
| | sur. B | BLAUNON LPE1007 | 1 |
| | | Wondersurf S-800 | 0.3 |
| (16) | sur. A | Unisafe A-LE | 0.06 |
| | sur. B | Noigen TDS-80 | 1 |
| (17) | sur. A | Unisafe A-LE | 0.06 |
| | sur. B | EMALEX OD-16 | 1 |
| (18) | sur. A | Unisafe A-LE | 0.06 |
| | sur. B | Wondersurf S-800 | 1 |
| (19) | sur. A | Unisafe A-LE | 0.06 |
| | sur. B | Nonion NS-210 | 1 |
| (20) | sur. A | Unisafe A-LE | 0.06 |
| | sur. B | Nonion NS-215 | 1 |
| (21) | sur. A | Unisafe A-LE | 0.06 |
| | sur. B | Acronecess KP-189R | 1 |
| (22) | sur. A | Unisafe A-LE | 0.06 |
| | sur. B | Newcol 2607 | 1 |
| (23) | sur. A | Unisafe A-LE | 0.06 |
| | sur. B | Newpol PE-64 | 1 |
| (24) | sur. A | Unisafe A-LE | 0.06 |
| | sur. B | Pluronic P-85 | 1 |
| (25) | sur. A | Newcol 723-SF | 0.1 |
| | sur. B | Noigen TDS-80 | 1 |
| (26) | sur. A | Newcol 723-SF | 0.1 |
| | sur. B | Noigen TDS-120 | 1 |
| (27) | sur. A | Newcol 723-SF | 0.1 |
| | sur. B | Wondersurf S-800 | 1 |
| (28) | sur. A | Newcol 723-SF | 0.1 |
| | sur. B | Wondersurf S-1400 | 1 |
| (29) | sur. A | Newcol 723-SF | 0.1 |
| | sur. B | Nonion NS-210 | 1 |
| (30) | sur. A | Newcol 723-SF | 0.1 |
| | sur. B | Emulgen A-60 | 1 |
| (31) | sur. A | Newcol 723-SF | 0.1 |
| | sur. B | BLAUNON DSP-12.5 | 1 |
| (32) | sur. A | Newcol 723-SF | 0.1 |
| | sur. B | Newcol 707F | 1 |
| (33) | sur. A | Newcol 723-SF | 0.1 |
| | sur. B | Pluronic P-85 | 1 |
| (34) | sur. A | Newcol 723-SF | 0.1 |
| | sur. B | BLAUNON LPE1007 | 1 |

Example 2

Four lipoprotein fractions of HDL (specific gravity: 1.063 or more), sdLDL (specific gravity: 1.044 to 1.063), LgLDL (specific gravity: 1.006 to 1.044) and VLDL and CM (specific gravity: 1.006 or less) were separated from human serum according to the ultracentrifugation method described in "Shin Seikagaku Jikken Koza 4" (New Lectures on Biochemical Experiments 4) (Tokyo Kagaku Dojin), and the reactivity of cholesterol in each lipoprotein fraction was calculated using the kits of Example 1.

(1) Calculation of "Reaction Absorbance" for Each Lipoprotein Fraction Obtained by Reaction of Cholesterol in Each Lipoprotein Fraction with the Kits of Example 1

The "reaction absorbance" was calculated according to the following procedure using Hitachi-7170S autoanalyzer.

Each lipoprotein fraction was added as a sample to a reaction cell (2 μL) and then the first reagent of each of the kits of Example 1 (0.15 mL) was added to initiate the reaction (first reaction), followed by heating at 37° C. for 5 minutes. The absorbance of the reaction solution after 5 minutes of reaction (E1) was measured at a main wavelength of 600 nm and a sub-wavelength of 700 nm. Then, to this reaction solution was added the second reagent of each of the kits of Example 1(1) to 1(34) (0.05 mL), followed by further heating at 37° C. for 5 minutes to carry out the reaction (second reaction). The absorbance of the reaction solution 5 minutes after the second reaction (E2) was measured at a main wavelength of 600 nm and a sub-wavelength of 700 nm, and the change in absorbance ($\Delta E'_{lipoprotein\ fraction}$) was calculated by subtracting E1 from E2. A similar measurement was carried out using a physiological saline solution as a sample in place of each lipoprotein fraction and the change in absorbance ($\Delta E'_{blank}$) was calculated. Finally, "reaction absorbance 3" for each lipoprotein fraction was calculated according to the following (equation 3).

Reaction absorbance $3 = \Delta E'_{lipoprotein\ fraction} - \Delta E_{blank}$     (equation 3)

(2) Calculation of Reactivity of Cholesterol in Each Lipoprotein Fraction

"Reaction absorbance 4" was calculated in a similar manner to (1) except that a kit for determination of total cholesterol, Determiner C TC (Kyowa Medex Co., Ltd.), was used in place of the kit of Example 1, with Hitachi-7170S autoanalyzer. The reactivity (%) of cholesterol in each lipoprotein fraction for each of the kits of Example 1(1) to 1(34) was calculated according to the following (equation 4). "Reaction absorbance 4" calculated in the measurement using Determiner C TC means the "reaction absorbance" when all of the cholesterol in the target lipoprotein reacted.

Reactivity (%) = Reaction absorbance 3/Reaction absorbance 4×100     (equation 4)

The reactivity of cholesterol in each lipoprotein fraction for each of the kits of Example 1(1) to 1(34) are shown in Table 2, wherein "−" indicates the reactivity of 1 to 10%, "±" indicates the reactivity of 10 to 20%, "+" indicates the reactivity of 20 to 50%, "++" indicates the reactivity of 50 to 80%, and "+++" indicates the reactivity of 80 to 100%.

As shown in Table 2, it was revealed that the kits of Example 1(1) to 1(34) can be used for the determination of sdLDL-C.

Example 3

Kits for determination of sdLDL-C consisting of the following first reagent and second reagent were prepared. The kits prepared using surfactants A and surfactants B shown in Table 3 were designated as kits of Example 3(35) to 3(44), respectively.

| First reagent | |
|---|---|
| MOPS (pH 7.0) | 20 mmol/L |
| EMSE | 0.3 g/L |
| Sodium sulfate | 2 g/L |
| Surfactant A (hereinafter abbreviated as "sur. A") | |
| LPL3 | 100 kU/L |
| CHO-PEL | 1 kU/L |
| Peroxidase | 10 kU/L |
| BSA | |

| Second reagent | |
|---|---|
| MOPS (pH 7.0) | 20 mmol/L |
| 4-Aminoantipyrine | 0.3 g/L |
| Peroxidase | 20 kU/L |

Surfactant B (hereinafter abbreviated as "sur. B")

TABLE 2

| Kit | Lipoprotein fraction | | | |
|---|---|---|---|---|
| | HDL | sdLDL | LgLDL | VLDL/CM |
| Example 1(1) | − | ++ | ± | − |
| Example 1(2) | − | ++ | − | − |
| Example 1(3) | − | +++ | + | − |
| Example 1(4) | − | ++ | ± | − |
| Example 1(5) | − | ++ | ± | − |
| Example 1(6) | − | +++ | + | − |
| Example 1(7) | − | +++ | + | − |
| Example 1(8) | − | ++ | ± | − |
| Example 1(9) | − | +++ | + | − |
| Example 1(10) | − | ++ | ± | − |
| Example 1(11) | − | ++ | ± | − |
| Example 1(12) | − | ++ | ± | − |
| Example 1(13) | − | +++ | ± | − |
| Example 1(14) | − | ++ | ± | ± |
| Example 1(15) | − | ++ | ± | − |
| Example 1(16) | − | ++ | ± | − |
| Example 1(17) | − | ++ | ± | − |
| Example 1(18) | − | ++ | ± | − |
| Example 1(19) | − | ++ | ± | − |
| Example 1(20) | − | ++ | ± | − |
| Example 1(21) | − | ++ | ± | − |
| Example 1(22) | − | ++ | ± | − |
| Example 1(23) | − | ++ | ± | − |
| Example 1(24) | − | ++ | ± | − |
| Example 1(25) | − | ++ | ± | − |
| Example 1(26) | − | ++ | ± | − |
| Example 1(27) | − | ++ | ± | − |
| Example 1(28) | − | ++ | ± | − |
| Example 1(29) | − | ++ | ± | − |
| Example 1(30) | − | ++ | ± | − |
| Example 1(31) | − | ++ | ± | − |
| Example 1(32) | − | ++ | ± | − |
| Example 1(33) | − | ++ | ± | − |
| Example 1(34) | − | ++ | ± | − |

TABLE 3

| # | | Constituent | Concentration (g/L) |
|---|---|---|---|
| (35) | sur. A | Unisafe A-LE | 0.3 |
| | sur. B | BLAUNON LPE1007 | 1 |
| | | Wondersurf S-800 | 0.3 |
| (36) | sur. A | Adeka Pluronic TR-704 | 1 |
| | sur. B | BLAUNON LPE1007 | 1 |
| | | Wondersurf S-800 | 0.3 |
| (37) | sur. A | Newcol 707-SF | 0.5 |
| | sur. B | BLAUNON LPE1007 | 1 |
| | | Wondersurf S-800 | 0.3 |
| (38) | sur. A | Pionin D-3110 | 0.1 |
| | sur. B | BLAUNON LPE1007 | 1 |
| | | Wondersurf S-800 | 0.3 |
| (39) | sur. A | Nymeen L-207 | 0.1 |
| | sur. B | BLAUNON LPE1007 | 1 |
| | | Wondersurf S-800 | 0.3 |
| (40) | sur. A | Unisafe A-LE | 0.3 |
| | | Pionin D-3120 | 0.1 |
| | sur. B | BLAUNON LPE1007 | 1 |
| | | Wondersurf S-800 | 0.3 |
| (41) | sur. A | Adeka Pluronic TR-704 | 1 |
| | | Pionin D-3120 | 0.05 |
| | sur. B | BLAUNON LPE1007 | 1 |
| | | Wondersurf S-800 | 0.3 |
| (42) | sur. A | Unisafe A-LE | 0.5 |
| | sur. B | BLAUNON LPE1007 | 1 |
| | | Wondersurf S-800 | 0.3 |
| | BSA | | 3 |
| (43) | sur. A | Newcol 707-SF | 0.3 |
| | sur. B | BLAUNON LPE1007 | 1 |
| | | Wondersurf S-800 | 0.3 |
| | BSA | | 3 |
| (44) | sur. A | Newcol 707-SF | 0.3 |
| | | Pionin D-3120 | 0.05 |

TABLE 3-continued

| # | | Constituent | Concentration (g/L) |
|---|---|---|---|
| | sur. B | BLAUNON LPE1007 | 1 |
| | | Wondersurf S-800 | 0.3 |
| | BSA | | 3 |
| (45) | sur. A | Uniol D-700 | 7 |
| | sur. B | Nonion NS-210 | 1 |
| | BSA | | 3 |
| (46) | sur. A | Pluronic 25R-2 | 0.3 |
| | sur. B | Nonion NS-210 | 1 |
| | BSA | | 3 |
| (47) | sur. A | Unilube 50MB-26 | 20 |
| | sur. B | Nonion NS-210 | 1 |
| | BSA | | 3 |

Example 4

The reaction absorbance for each of 24 human serum samples was measured in a manner similar to the measurement method described in Example 2 (1) using the kits of Example 3(35) to 3(47) with Hitachi-7170S autoanalyzer.

Subsequently, the serum samples were subjected to centrifugation by the ultracentrifugation method described in Journal of Lipid Research, vol. 44, p. 2193-2201 (2003) to separate the sdLDL fraction of the samples. The amount of cholesterol in the obtained sdLDL fraction was measured using Determiner L TCII (Kyowa Medex Co., Ltd.). The correlation coefficients between the measurement values in the measurements using the kits of Example 3(35) to 3(47) and the measurement values by the ultracentrifugation method are shown in Table 4.

TABLE 4

| Kit | Correlation coefficient to the ultracentrifugation method |
|---|---|
| Example 3(35) | 0.871 |
| Example 3(36) | 0.888 |
| Example 3(37) | 0.912 |
| Example 3(38) | 0.864 |
| Example 3(39) | 0.890 |
| Example 3(40) | 0.902 |
| Example 3(41) | 0.915 |
| Example 3(42) | 0.919 |
| Example 3(43) | 0.916 |
| Example 3(44) | 0.927 |
| Example 3(45) | 0.886 |
| Example 3(46) | 0.876 |
| Example 3(47) | 0.856 |

As shown in Table 4, the measurement results obtained by using the kits of Example 3(35) to 3(47) showed a good correlation with those obtained by the ultracentrifugation method.

Further, from the comparison of the measurements using the kits of Example 3(42) and 3(43) which comprise BSA in the first reagent with those using the kits of Example 3(35) and 3(37), it was revealed that the use of a kit comprising BSA in the first reagent improves the correlation with the ultracentrifugation method compared with the use of a kit which does not comprise BSA in the first reagent.

Example 5

Kits for determination of sdLDL-C consisting of the following first reagent and second reagent were prepared. The kits prepared using surfactants A and surfactants B shown in Table 5 were designated as kits of Example 5(48) to 5(57), respectively.

| First reagent | |
|---|---|
| MOPS (pH 7.0) | 20 mmol/L |
| EMSE | 0.3 g/L |
| Sodium sulfate | 2 g/L |
| Peroxidase | 10 kU/L |
| BSA | 3 g/L |

Surfactant A (hereinafter abbreviated as "sur. A")
Cholesterol ester hydrolase (hereinafter abbreviated as "CHER")
Cholesterol oxidase (hereinafter abbreviated as "CHOD")

| Second reagent | |
|---|---|
| MOPS (pH 7.0) | 20 mmol/L |
| 4-Aminoantipyrine | 0.3 g/L |
| Peroxidase | 20 kU/L |
| BLAUNON LPE-1007 | 1 g/L |
| Wondersurf S-800 | 0.3 g/L |

TABLE 5

| # | | Constituent | Concentration | |
|---|---|---|---|---|
| (48) | sur. A | Newcol 707-SF | 0.5 | g/L |
| | CHER | LP | 300 | kU/L |
| | CHOD | CHO-PEL | 1 | kU/L |
| (49) | sur. A | Newcol 707-SF | 0.5 | g/L |
| | CHER | LPAP | 200 | kU/L |
| | CHOD | CHO-PEL | 1 | kU/L |
| (50) | sur. A | Newcol 707-SF | 0.2 | g/L |
| | CHER | LIPS | 400 | kU/L |
| | CHOD | CHO-PEL | 1 | kU/L |
| (51) | sur. A | Newcol 707-SF | 0.5 | g/L |
| | CHER | LPL3 | 300 | kU/L |
| | CHOD | CHO-CE | 1 | kU/L |
| (52) | sur. A | Newcol 707-SF | 0.7 | g/L |
| | CHER | LP | 300 | kU/L |
| | CHOD | CHO-CE | 1 | kU/L |
| (53) | sur. A | Newcol 707-SF | 0.7 | g/L |
| | CHER | LPL3 | 300 | kU/L |
| | CHOD | COO-322 | 1 | kU/L |
| (54) | sur. A | Newcol 707-SF | 0.7 | g/L |
| | CHER | LP | 300 | kU/L |
| | CHOD | COO-322 | 1 | kU/L |
| (55) | sur. A | Newcol 707-SF | 0.7 | g/L |
| | | Uniol D-700 | 7 | g/L |
| | CHER | LP | 300 | kU/L |
| | CHOD | COO-322 | 1 | kU/L |
| (56) | sur. A | Newcol 707-SF | 0.7 | g/L |
| | | Pluronic 25R-2 | 0.7 | g/L |
| | CHER | LP | 300 | kU/L |
| | CHOD | COO-322 | 1 | kU/L |
| (57) | sur. A | Newcol 707-SF | 0.7 | g/L |
| | | Unilube 50MB-26 | 10 | g/L |
| | CHER | LP | 300 | kU/L |
| | CHOD | COO-322 | 1 | kU/L |

Example 6

The reaction absorbance for each of 25 human serum samples was measured in a manner similar to the method described in Example 2 (1) using the kits of Example 3(43) and Examples 5(48) to 5(57) with Hitachi-7170S autoanalyzer.

Subsequently, the serum samples were subjected to centrifugation by the ultracentrifugation method described in Journal of Lipid Research, vol. 44, p. 2193-2201 (2003) to separate the sdLDL fraction of the samples. The amount of cholesterol in the obtained sdLDL fraction was measured using Determiner L TCII (Kyowa Medex Co., Ltd.). The correlation coefficients between the measurement values in the measurements using the kits of Example 3(43) and Examples 5(48) to 5(57) and the measurement values by the ultracentrifugation method are shown in Table 6.

TABLE 6

| Kit | Correlation coefficient to the ultracentrifugation method |
|---|---|
| Example 3(43) | 0.914 |
| Example 5(48) | 0.949 |
| Example 5(49) | 0.914 |
| Example 5(50) | 0.887 |
| Example 5(51) | 0.935 |
| Example 5(52) | 0.969 |
| Example 5(53) | 0.928 |
| Example 5(54) | 0.880 |
| Example 5(55) | 0.918 |
| Example 5(56) | 0.924 |
| Example 5(57) | 0.897 |

As shown in Table 6, the measurement results obtained by using the kits of Example 3(43) and Example 5(48) to 5(57) showed a good correlation with those obtained by the ultracentrifugation method.

Example 7

Kits for determination of sdLDL-C consisting of the following first reagent and second reagent were prepared. The kits prepared using surfactants A and surfactants B shown in Table 7 were designated as kits of Examples 7(58) to 7(67), respectively.

| First reagent | |
|---|---|
| MOPS (pH 7.0) | 20 mmol/L |
| EMSE | 0.3 g/L |
| Sodium sulfate | 2 g/L |
| Surfactant A (hereinafter abbreviated as "sur. A") | |
| LPL3 | 100 kU/L |
| CHO-PEL | 1 kU/L |
| Peroxidase | 10 kU/L |
| BSA | |

| Second reagent | |
|---|---|
| MOPS (pH 7.0) | 20 mmol/L |
| 4-Aminoantipyrine | 0.3 g/L |
| Peroxidase | 20 kU/L |
| Surfactant B (hereinafter abbreviated as "sur. B") | |

TABLE 7

| # | | Constituent | Concentration (g/L) |
|---|---|---|---|
| (58) | sur. A | Adeka Pluronic TR-704 | 1 |
| | sur. B | Noigen TDS-80 | 1 |
| (59) | sur. A | Adeka Pluronic TR-704 | 1 |
| | sur. B | Noigen TDS-120 | 1 |
| (60) | sur. A | Adeka Pluronic TR-704 | 1 |
| | sur. B | EMALEX OD-16 | 1 |
| (61) | sur. A | Adeka Pluronic TR-704 | 1 |
| | sur. B | Nonion NS-210 | 1 |
| (62) | sur. A | Adeka Pluronic TR-704 | 1 |
| | sur. B | Wondersurf S-800 | 1 |

TABLE 7-continued

| # | | Constituent | Concentration (g/L) |
|---|---|---|---|
| (63) | sur. A | Adeka Pluronic TR-704 | 1 |
| | sur. B | Emulgen A-60 | 1 |
| (64) | sur. A | Newcol 707-SF | 0.3 |
| | sur. B | Noigen TDS-80 | 1 |
| | BSA | | 3 |
| (65) | sur. A | Newcol 707-SF | 0.3 |
| | sur. B | Noigen TDS-120 | 1 |
| | BSA | | 3 |
| (66) | sur. A | Newcol 707-SF | 0.3 |
| | sur. B | Nonion NS-210 | 1 |
| | BSA | | 3 |
| (67) | sur. A | Newcol 707-SF | 0.3 |
| | sur. B | Emulgen A-60 | 1 |
| | BSA | | 3 |

Example 8

The reaction absorbance for each of 21 human serum samples was measured in a manner similar to the method described in Example 2 (1) using the kits of Example 3(36) and Example 7(58) to 7(67).

Subsequently, the serum samples were subjected to centrifugation by the ultracentrifugation method described in Journal of Lipid Research, vol. 44, p. 2193-2201 (2003) to separate the sdLDL fraction of the serum. The amount of cholesterol in the obtained sdLDL fraction was measured using Determiner L TCII (Kyowa Medex Co., Ltd.). The correlation coefficients between the measurement values in the measurements using the kits of Examples and Comparative Examples and the measurement values by the ultracentrifugation method are shown in Table 8.

TABLE 8

| Kit | Correlation coefficient to the ultracentrifugation method |
|---|---|
| Example 3(36) | 0.889 |
| Example 7(58) | 0.925 |
| Example 7(59) | 0.879 |
| Example 7(60) | 0.922 |
| Example 7(61) | 0.915 |
| Example 7(62) | 0.908 |
| Example 7(63) | 0.890 |
| Example 7(64) | 0.933 |
| Example 7(65) | 0.931 |
| Example 7(66) | 0.914 |
| Example 7(67) | 0.932 |

As shown in Table 8, the measurement results obtained by using the kits of Example 3(36) and Example 7(58) to 7(67) showed a good correlation with those obtained by the ultracentrifugation method.

Example 9

Determination of sdLDL-C in a Sample sdLDL-C in each of fresh human serum samples (2 samples) was measured in the following manner using the ultracentrifugation method and the kits of Example 3(36) and Example 3(44) of the present invention.
(1) Determination of sdLDL-C in Human Serum Samples Using the Ultracentrifugation Method The human serum samples (2 samples) were subjected to centrifugation by the ultracentrifugation method described in Journal of Lipid Research, vol. 44, p. 2193-2201 (2003) to separate the sdLDL fraction of the serum. The amount of cholesterol in the obtained sdLDL fraction was measured using Determiner L TCII (Kyowa Medex Co., Ltd.).

(2) Preparation of a Calibration Curve

A standard serum solution found to have an sdLDL-C concentration of 43.1 mg/dL by the measurement by the ultracentrifugation method was used as a sample for preparation of a calibration curve. In a manner similar to the measurement method described in Example 2 (1), the reaction absorbance of the sample for preparation of a calibration curve was measured with Hitachi-7170S autoanalyzer using the kits of Example 3(36) and Example 3(44). A calibration curve for each kit was prepared based on the relationship between the measured reaction absorbance and the sdLDL-C concentration in the sample for preparation of a calibration curve.

(3) Determination of sdLDL-C in the Two Human Serum Samples

A reaction was carried out in the same manner as in the above (2), except that two human serum samples were used in place of the sample for preparation of a calibration curve, for each of the two samples, and the concentration of sdLDL-C in each of the samples was determined from the absorbance of the reaction solution after the reaction and the calibration curve prepared in the above (2) with respect to each kit.

The sdLDL-C concentration in each of the two samples determined by the ultracentrifugation method in the above (1) and the sdLDL-C concentration therein determined by the measurements using the kits of Example 3(36) and Example 3(44) in the above (3) are shown in Table 9.

TABLE 9

| | sdLDL-C Concentration (mg/dL) | | |
|---|---|---|---|
| | Ultracentrifugation method | Example 3(36) | Example 3(44) |
| Serum 1 | 88.2 | 87.3 | 85.8 |
| Serum 2 | 31.9 | 31.7 | 29.5 |

Table 9 demonstrates that sdLDL-C in human serum can be accurately determined by the method of the present invention using the kit of the present invention.

INDUSTRIAL APPLICABILITY

The present invention provides a method and a kit for determination of cholesterol in small dense low-density lipoprotein useful for the diagnosis of coronary diseases such as arteriosclerosis.

The invention claimed is:

1. A method for determining cholesterol in a small dense low-density lipoprotein (hereinafter abbreviated sdLDL-C) in a sample, which comprises the steps:
   (i) obtaining a solution containing a surfactant selected from the group consisting of polyoxyethylene alkylamine, amine oxides, alkylbetaine, alkylammonio-1-propanesulfonate, acid amide alkylbetaine, polyoxyethylene benzyl alkyl quaternary ammonium salt, polyoxyethylene fatty acid amide, polyoxyethylene polycyclic phenyl ether sulfuric acid ester salt, polyoxyethylene alkylphenyl ether sulfuric acid ester salt, polyoxyethylene fatty acid amide sulfuric acid ester salt, polyoxyethylene alkylamine sulfuric acid ester salt, N-acyl taurine salt, N-acyl amino acid salt, ethylenediamine-polyoxyethylene polyoxypropylene condensate, polypropylene glycol derivative not including polyethylene glycol therein, polyoxyethylene polyoxypropylene condensate represented by formula (I):

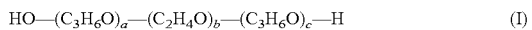
$$HO-(C_3H_6O)_a-(C_2H_4O)_b-(C_3H_6O)_c-H \quad (I)$$

(wherein a, b and c independently represent an integer of 1 to 200), and polyoxyethylene polyoxyalkylene alkyl ether (wherein the alkyl has 9 or fewer carbon atoms),
   (ii) reacting a combination of cholesterol ester hydrolase and cholesterol oxidase, or a combination of cholesterol ester hydrolase, cholesterol dehydrogenase and oxidized coenzyme with the solution to eliminate cholesterol in high-density lipoprotein (hereinafter abbreviated HDL-C), cholesterol in very low-density lipoprotein (hereinafter abbreviated VLDL-C), cholesterol in chylomicron (hereinafter abbreviated as CM-C) and cholesterol in large low-density lipoprotein (hereinafter abbreviated LgLDL-C) in the sample;
   (iii) adding a surfactant selected from the group consisting of polyoxyethylene alkyl ether, polyoxyethylene polyoxyalkylene alkyl ether (wherein the alkyl has at least 10 carbon atoms), polyoxyethylene alkylphenyl ether, polyoxyethylene polyoxyalkylene alkylphenyl ether, polyoxyethylene polycyclic phenyl ether, polyoxyethylene polyoxyalkylene polycyclic phenyl ether, polyoxyethylene polyoxypropylene condensate represented by formula (II):

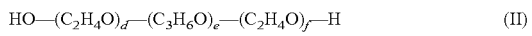
$$HO-(C_2H_4O)_d-(C_3H_6O)_e-(C_2H_4O)_f-H \quad (II)$$

(wherein d, e and f independently represent an integer of 1 to 200), and polyoxyethylene polyoxyalkylene alkylamine to form hydrogen peroxide or reduced coenzyme, and measuring the formed hydrogen peroxide or reduced coenzyme; and
   (iv) determining a sdLDL-C concentration in the sample by carrying out the above steps (i) to (iii) using a standard sample with a known concentration of sdLDL-C to form hydrogen peroxide or reduced coenzyme, measuring the formed hydrogen peroxide or reduced coenzyme, correlating the sdLDL-C concentration with a measurement value on the hydrogen peroxide or reduced coenzyme, so as thereby to determine a sdLDL-C concentration in the sample.

2. The method according to claim 1, wherein step (i) is carried out in the presence of albumin.

3. The method according to claim 1, wherein the concentration of the surfactant in step (ii) is 0.0001 to 1%, and the concentration of the surfactant in step (iii) is 0.001 to 5%.

* * * * *